(12) United States Patent
Takoudis et al.

(10) Patent No.: US 6,818,894 B2
(45) Date of Patent: Nov. 16, 2004

(54) METHOD AND APPARATUS FOR CHARACTERIZATION OF ULTRATHIN SILICON OXIDE FILMS USING MIRROR-ENHANCED POLARIZED REFLECTANCE FOURIER TRANSFORM INFRARED SPECTROSCOPY

(75) Inventors: Christos G. Takoudis, Oak Park, IL (US); Zhenjiang Cui, Santa Clara, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 66 days.

(21) Appl. No.: 10/134,333

(22) Filed: Apr. 29, 2002

(65) Prior Publication Data

US 2002/0180991 A1 Dec. 5, 2002

Related U.S. Application Data

(60) Provisional application No. 60/287,461, filed on Apr. 30, 2001.

(51) Int. Cl.[7] ............................................... G01J 5/08
(52) U.S. Cl. .......................... 250/339.08; 250/339.07; 250/339.06; 250/339.01; 250/338.1; 250/336.1
(58) Field of Search ...................... 250/339.08, 339.07, 250/339.06, 339.01, 338.1, 336.1

(56) References Cited

U.S. PATENT DOCUMENTS

| | | | | |
|---|---|---|---|---|
| 5,108,540 A | * | 4/1992 | Frijlink ........................ | 117/98 |
| 5,321,264 A | * | 6/1994 | Kuwabara et al. ...... | 250/339.11 |
| 5,381,234 A | | 1/1995 | Barbee et al. .............. | 356/369 |
| 5,534,698 A | * | 7/1996 | Ohshima et al. ........ | 250/339.11 |
| 5,900,633 A | | 5/1999 | Solomon et al. ........ | 250/339.08 |
| 6,169,289 B1 | * | 1/2001 | White et al. ............. | 250/458.1 |
| 6,200,201 B1 | * | 3/2001 | Ravkin et al. ................ | 451/65 |
| 6,277,657 B1 | * | 8/2001 | Nozawa et al. ................ | 438/8 |
| 6,558,802 B1 | * | 5/2003 | Henley et al. .............. | 428/446 |
| 6,577,926 B1 | * | 6/2003 | Chang et al. ............... | 700/274 |

FOREIGN PATENT DOCUMENTS

| | | |
|---|---|---|
| EP | 0 874 396 A2 | 10/1998 |
| EP | 1 039 514 A1 | 9/2000 |

OTHER PUBLICATIONS

Stefanov, Boris B., et al.; "Silicon Epoxide: Unexpected Intermediate During Silicon Oxide Formation;" The American Physical Society, Nov. 2, 1998, vol. 81, No. 18, pp. 3908–3911.

(List continued on next page.)

*Primary Examiner*—David Porta
*Assistant Examiner*—Christine Sung
(74) *Attorney, Agent, or Firm*—Marshall, Gerstein & Borun LLP

(57) ABSTRACT

Ultrathin silicon oxide films thermally grown on Si(100) are characterized with Mirror-Enhanced Polarized Reflectance Fourier Transform Infrared spectroscopy (MEPR-FTIR). MEPR-FTIR is proposed to effectively probe properties of ultra-thin films. Using a mirror and a polarizer, MEPR-FTIR overcomes the difficulty of weak IR intensities normally encountered in ultrathin gate dielectrics such as $SiO_2$ and the intensity of the silicon oxide longitudinal optical (LO) mode is found to increase by a factor of about 20. Therefore, FTIR spectrometers with sensitivity down to 0.01% may allow even sub-monolayer probing of silicon oxide on Si substrates.

32 Claims, 15 Drawing Sheets

OTHER PUBLICATIONS

Ohshima, Hisayoshi, et al.; "High Sensitivity FT–IR–RAS for Silicon Surface Study;" 1994 Materials Research Society, vol. 318, pp. 413–418.

Queeney, K.T., et al., "Infrared Spectroscopic Analysis of the Si/SiO2 Interface Structure of Thermally Oxidized Silicon;" Journal of Applied Physics, vol. 87, No. 3, Feb. 1, 2000, pp. 1322–1330.

Koller. Kent B., et al.; "In Situ Infrared Reflection Absorption Spectroscopic Characterization of Plasma Enhanced Chemical Vapor Deposited SiO2 Films;" J. Appl. Phys. 64(9), Nov. 1, 1988, pp. 4704–4710.

Fujimura, Shuzo et al., "Observation of Thin SiO2 Films Using IR–RAS;" *The Physics and Chemistry of SiO2 and the Si–SiO2 Interface 2*; Plenum Press, New York, 1993, pp. 91–98.

International Search Report in International (PCT) Application No. PCT/US02/13460 dated Oct. 4, 2002.

* cited by examiner

OSO·M

S·M

OSO

S

M

METHOD AND APPARATUS FOR CHARACTERIZATION OF ULTRATHIN SILICON OXIDE FILMS USING MIRROR-ENHANCED POLARIZED REFLECTANCE FOURIER TRANSFORM INFRARED SPECTROSCOPY

CROSS-REFERENCE TO RELATED APPLICATION

This application claims the benefit under 35 U.S.C. §119 (e) of U.S. provisional application Ser. No. 60/287,461 filed Apr. 30, 2001.

BACKGROUND

The present invention relates to a method and apparatus for characterizing films grown on a silicon substrate using infrared spectroscopy and, more particularly, to characterization of ultra thin silicon oxide films thermally grown on silicon using mirror-enhanced polarized reflectance Fourier Transform Infrared (MEPR-FTIR) Spectroscopy.

The timely achievement of evolving requirements of the National Technology Roadmap for Semiconductors requires a paradigm shift in the role of metrology from off-line sampling to on-line control. Future integrated circuit (IC) technologies will use thinner gate dielectrics. Therefore, non-destructive in-situ probing and characterization of ultrathin (<50 Å) dielectric layers such as $SiO_2$, $Si_3N_4$, $SiN_xO_y$ and even $Ta_2O_5$ in real time is highly desirable.

As a non-destructive optical characterization technique, Fourier Transform InfraRed (FTIR) Spectroscopy and Ellipsometry offer sensitive, non-contact techniques that provide surface information as well as bulk material information. Other sensitive and convenient characterization methods include contact angle measurement where the contact angles of water or other solvents reflect the surface criterion directly; that is, surface free energy. FTIR spectroscopy has been used successfully in detecting interstitial oxygen, nitrogen, boron and other impurities in silicon wafers as well as probing adsorbed species on semiconductor surfaces. Since fabrication-compatible FTIR systems have already been used in measuring epitaxial layer thickness, their capabilities in probing and characterizing gate dielectrics are expected to expand in future technologies.

Historically, FTIR spectroscopy had been used to measure film properties via the modes of interferometry, transmission, attenuated total reflectance (ATR) and reflectance. Except for ATR, which can be used for ultrathin film characterization but is not preferred for in-situ applications and requires specially prepared substrates, all others are more effective for relatively thick dielectric layers. A study on silicon oxides down to 6 Å was recently reported to use dynamically aligned FTIR spectroscopy in single pass external transmission geometry (See K. T. Queeny et al., J. Appl. Phys. 87, 1322 (2000) and B. B. Stefanov et al., Phys. Rev. Lett. 81, 3908 (1998)). For the integration and use of FTIR into the front end characterization metrology of current and future developed ultra-thin gate dielectrics, the development of in-situ FTIR modes for routine probing and characterization of films a few monolayers thick would be desirable.

Ellipsometry has been used for thin film, surface and bulk material characterization of dielectric films typically thicker than about 30 Å. For dielectric films thinner than 30 Å, further work has been conducted by the National Institute of Standards and Technologies and various tool manufacturers in order to enhance the accuracy and repeatability so that widely accepted standards can be set up. Taking advantage of Fourier transform spectroscopy over the infrared range, infrared ellipsometry has recently shown the ability of probing the film morphology from the dielectric function, and the microstructure from the vibrational absorption.

Reflectance IR has been related to thickness characterization because of its in-situ adaptability. However, because of the relatively weak IR intensity it is seldom used in films less than 50 Å thick.

The sensitivity and selectivity of double modulation FTIR reflection absorption spectroscopy for absorbing species on a reflecting surface has been reported to provide adequate signal-to-noise in a short time; one such application has been the in situ analysis of low-temperature plasma-enhanced chemical vapor deposition of $SiO_2$ films on silicon, and aluminum substrates. (see e.g., Koller et al., J. Appl. Phys. 64, 4704 (1988)). It has also been previously reported that with attachment of a reflective mirror to a single polished or double polished wafer, the Si—O bond at about 1250 $cm^{-1}$ of a thin chemically oxidized layer on Si(111) surfaces could be detected (see e.g., Ohshina et al., *Interface control of electrical, chemical, and mechanical properties: Symposium held Nov. 29–Dec. 3, 1993, Boston, Mass., U.S.A.* (Materials Research Society, Pittsburgh, 1994, p. 413). Here, however, an air gap between the attached mirror and sample wafer was reported as the reason for the observed IR intensity, the intensity of the IR peaks was weak even with a very sensitive detector (i.e., MCT) and the probing was performed ex-situ.

DESCRIPTION OF THE PRESENTLY PREFERRED EXAMPLES

An apparatus and method for overcoming the limitations of conventional FTIR spectroscopy using Mirror-Enhanced Polarized Reflectance (MEPR) FTIR, which is capable of in-situ or ex-situ probing, is disclosed. The use of MEPR-FTIR has been shown to result in enhancements of the reflectance IR intensity of ultrathin gate dielectric films by a factor of about 20. The MEPR-FTIR intensity-film thickness relationship for silicon oxide films down to one monolayer thick can thus be routinely achieved. Theoretical simulations based on the general Fresnel function are also disclosed and compared with experimental data.

In an example system, an FTIR spectrometer is provided, such as a Nicolet Magna-IR 560 with a standard deuterated triglycine sulfate (DTGS) detector and a KBr beamsplitter or a HgCdTe (MCT-A) detector. The spectral range of the spectrometer is approximately 400 $cm^{-1}$ to 4000 $cm^{-1}$, with a standard nominal spectral resolution of 0.50 $cm^{-1}$. A signal-to-noise ratio of 30000/1 is desired for one minute at 4 $cm^{-1}$ resolution. P- and S-polarized beams are obtained using a ZnSe wire grid polarizer, such as a polarizer manufactured by Spectra-Tech Inc. A fixed 80° grazing angle accessory FT-80 may be used for specular reflectance with gold-coated optics. The IR intensity is expressed as 100× (1−R), where the reflectance R is the ratio of the intensity reflected from the sample to the intensity reflected from the background.

The Si wafer samples (resistance 5–100 Ω-cm) used are approximately 200 μm thick and have crystallographic directions of 100, in this example. Although the disclosed wafer samples are not double side polished in this example, they are found to be smoother than backside lapped wafers. Before the thermal growth of $SiO_2$, all wafer samples are cleaned in Summa Clean (a mixture of choline and methanol) for 20 min at 40° C. to remove organic and inorganic contaminants. A 30 second dip in buffered HF ($NH_4F$:49% HF, 10:1) is used for the removal of the native oxide. The HF treated (oxide-free) samples are moved into a FTIR bench within 1 min and IR spectra are collected. Next, the samples are oxidized in air at a desired temperature for pre-specified times and IR spectra are collected. The native oxide is formed on Si wafer samples exposed to the lab ambient.

The oxide thickness may be obtained with a J. A. Woollam M-44 Spectral Ellipsometer operated at an incident angle of 75°. Cross-sectional transmission electron microscopy (XTEM) may be performed with a JEOL 10 Microscope (and a resolution of 1.6 Å). X-ray photoelectron spectroscopy (XPS) may be performed with a Kratos XSAM 800 system and an ion sputtering energy of 4 KV.

Figure 1A:
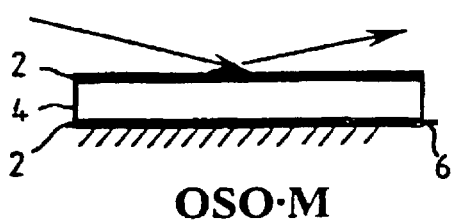
FIGS. 1A–1E illustrate schematic configurations of different Si (100) wafer samples where OSO—M is Si wafer sample with ultrathin (native or thermally grown) oxide on both sides and mirror on the one side in FIG. 1A; S.M is Si wafer attached to a mirror on the one side in FIG. 1B; OSO is Si wafer with ultrathin oxide on both sides in FIG. 1C; S is Si wafer sample only in FIG. 1D; and M is Mirror only in FIG. 1E.
Figure 1B:
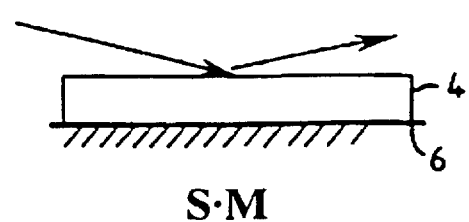
Figure 1C:
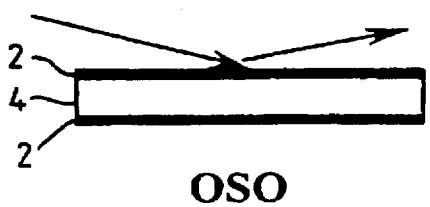
Figure 1D:
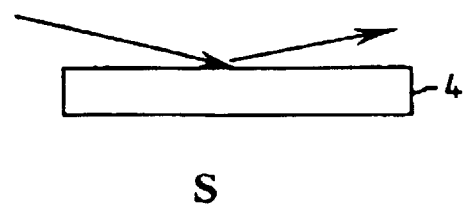
Figure 1E:
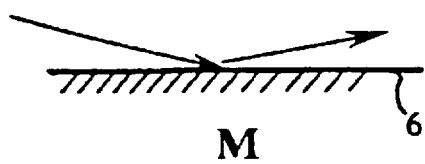

The basic configuration of the disclosed MEPR-FTIR spectroscopy is to place one side of a wafer sample against a mirror and simultaneously direct a polarized IR beam to the other side at a grazing angle (e.g., 80° to the normal). The mirror-attachment effect for five different configurations of the wafer samples is illustrated in FIGS. 1A–1E. The illustrated samples labeled OSO—M and S-M in FIGS. 1A and 1B are attached to a mirror, where "O" represents oxide film 2, "S" the Si substrate 4, and "M" the mirror 6. Illustrated samples OSO and S in FIGS. 1C and 1D are not attached to a mirror, and the illustration labeled M in FIG. 1E is just the mirror 6. The ultrathin oxides 2 of the silicon samples are shown schematically as the dark area at the top and bottom of the samples. It is noted that S-M and S in FIGS. 1B and 1D, respectively, are HF-treated oxide-free samples.

Attaching a mirror to the backside of the wafer sample substantially affects the IR intensity. This change in intensity may be probed with a single IR beam intensity set at 1583 $cm^{-1}$, for example, where the highest intensity is observed, and the absorption interference from the silicon sample is absent. The IR intensities observed at 1583 $cm^{-1}$ are 2.9 arbitrary units (a.u.) for the sample OSO—M in FIG. 1A, 2.1 a.u. for OSO in FIG. 1C, 2.7 a.u. for S-M in FIG. 1B, 1.9 a.u. for S in FIG. 1D, and 3.0 a.u. for M in FIG. 1E. Hence, when the mirror is attached to the backside of a sample, the IR intensity is increased by about 40% over those without attachment to the mirror. Indeed, the IR intensities of the samples attached to the mirror approach the highest intensity of the mirror alone (3.0 a.u.). Such enhancement can be appreciated by one skilled in the art to be the result of the redirection of a transmitted beam back into the detector (see also below), which is further illustrated by the presence of the bulk interstitial O—Si vibrational feature at 1106 $cm^{-1}$ (See FIG. 2). Hence, the use of such a configuration with a mirror attached to a wafer sample having silicon oxide layers to be probed, results in increased IR intensity.

Figure 2:
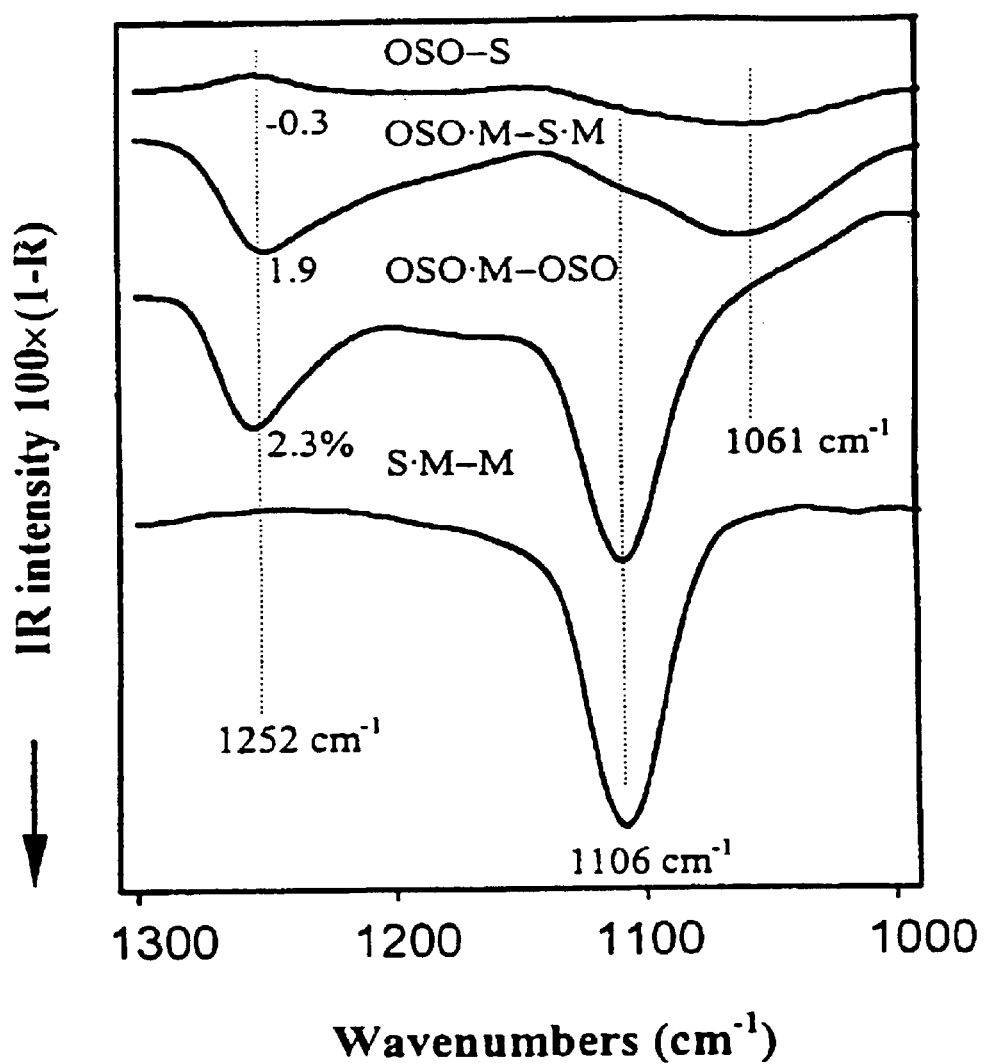
FIG. 2 illustrates IR spectra of 50 Å-thick native oxide samples shown schematically in FIG. 1. I–J is the spectrum of sample I with the spectrum of sample J as background. The 1252 $cm^{-1}$ intensity (in %) is also shown. No polarizer is used.

Further illustration of the mirror-attachment effect is presented in FIG. 2 for an oxide 50 Å (±1 Å) thick. The absorption feature at 1252 $cm^{-1}$ is assigned to the longitudinal optical (LO) mode of silicon oxide asymmetric stretching and the one at 1060 $cm^{-1}$ is assigned to the transverse optical (TO) mode of $SiO_2$ asymmetric stretching. Curve "OSO—S" shown in FIG. 2 is the spectrum from sample OSO shown in FIG. 1C with the oxide-free sample S as background. In the OSO—S spectrum (i.e., the OSO sample with the oxide-free samples as background), the TO feature is positive (e.g., downwards in the scale shown in FIG. 2). The LO mode, however, is shown to be negative with an intensity of about −0.3% (the detectable limit is 0.1%, here). Such weak IR intensities of the LO mode appear to be the main obstacle for the probing of ultrathin (<50 Å) film thickness and other properties.

For the negative LO mode in the OSO—S spectrum, detailed theoretical calculations (as will be described later) show that both the top and bottom oxide layers contribute to the negative LO mode, with the top layer (i.e., the layer facing the IR beam) mostly responsible. Even for a sample with top oxide only (i.e., no bottom oxide), the P-polarized IR beam with an incident angle larger than the Brewster angle (e.g., 73.6° in this particular example) would generate a negative peak at the LO mode frequency.

Contrary to the weak IR intensity of the OSO—S spectrum, the enhanced MEPR-FTIR intensities of an OSO.M sample with S.M and OSO sample as backgrounds, respectively, are shown in FIG. 2. A comparison of the OSO.M—S.M and OSO—S spectra in FIG. 2 illustrates two characteristics: the LO spectral feature changes from negative (in OSO—S) to positive (in OSO.M—S.M), and its intensity increases by a factor of about 6. Yet, the TO mode intensity is seen to increase by a factor of about 2. The OSO.M—OSO spectrum shows similar intensity enhancements for the LO and TO modes. The S.M—M spectrum illustrates only the interstitial vibrational feature, because there is no oxide on either S.M or M (see FIGS. 1B and 1E). Therefore, the mirror-attachment is seen to enhance the IR intensity by a factor of about 6 to 7.

Figure 3:
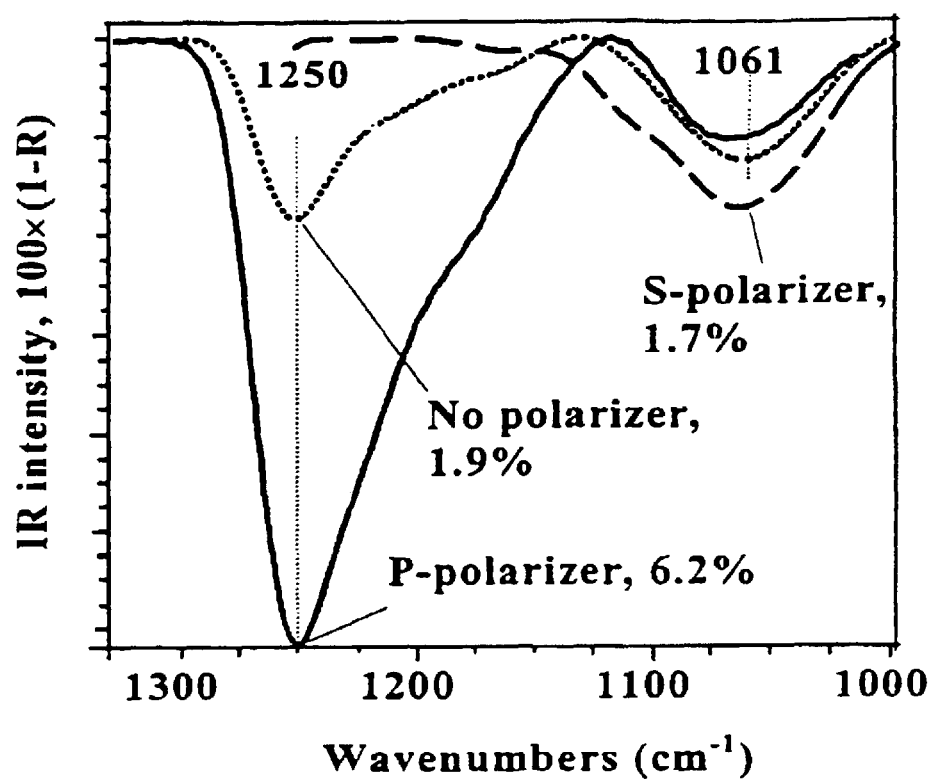
FIG. 3 illustrates IR spectra of sample OSO—M with P-, S-, and non-polarized beams.

The polarization effect on the enhancement of the IR intensity is probed by casting P-polarized (with electric field parallel to the incident plane), S-polarized (with electric field perpendicular to the incident plane) and non-polarized beams on the wafer sample. FIG. 3 illustrates the spectra of the sample OSO—M with P-, S- and no polarization. The IR intensity of the LO feature increases from 1.9% (with no polarization) to 6.2% (with P-polarization), that is, by a factor of about 3. In S-polarized beams, the LO mode is removed and the TO mode is only slightly increased from about 1.2% (with no polarization) to 1.7%. Such large P-polarization enhancements of the silicon oxide LO feature make it particularly advantageous and useful to exploit. In fact, the LO mode intensity in the presence of both a P-polarized beam and the mirror attachment is shown to be higher than that of the conventional specular reflectance spectrum OSO—S (i.e., without the MEPR-FTIR enhancement) by a factor of about 20 (FIGS. 2 and 3).

The enhanced IR intensity of the LO mode according to the present disclosure is attributable to four factors. Analyses of the single beam IR intensities from the samples OSO.M to M (see FIG. 1) indicate that part of the MEPR-FTIR enhancement comes from the increased beam intensity through the redirection of the transmitted beam back to the detector. In addition, the redirected transmitted beam includes the Si—O asymmetric stretching vibrational bonds not only from the top layer of the sample, but also from the bottom one. Third, the use of a P-polarized beam enhances the intensity of the LO mode. Finally, the highly reflective metal surface of the mirror produces a standing electric field that increases the absorption intensity of $SiO_2$ adjacent to it.

In order to experimentally determine IR intensity film thickness relationships, Silicon samples covered with different oxide films may be used in order to probe the LO mode intensity-film thickness relationships. One set of samples may have a native oxide formed at room temperature in a lab environment; two others have thermal oxide films grown at 400° C. and 1050° C., respectively. Oxides with different thickness may be prepared either by etching back the oxide layer (i.e., for the samples covered with either native oxide or the oxide formed at 1050° C.) or by appropriate oxidation of a Si wafer sample.

IR spectra may be then collected in the following manner. First, the IR spectrum of the sample is obtained with the P-polarized beam, while an IR spectrum with the S-polarized beam is used as background. In this process, much of the intensity of the TO mode is removed. Next, the spectrum of an HF dipped oxide-free sample is subtracted from the resultant above. Theoretically, as well as from experimental data shown in FIG. 3, it is unnecessary to take an S-polarized beam as background. However, in practice, this background processing may help remove much of the noise/interference from the probing environment, thus facilitating the accuracy of data collection. Hence, this background subtraction may indeed be useful for particular in-situ applications. However, information carried by the TO mode may also be relevant and should be considered.

Figure 4:
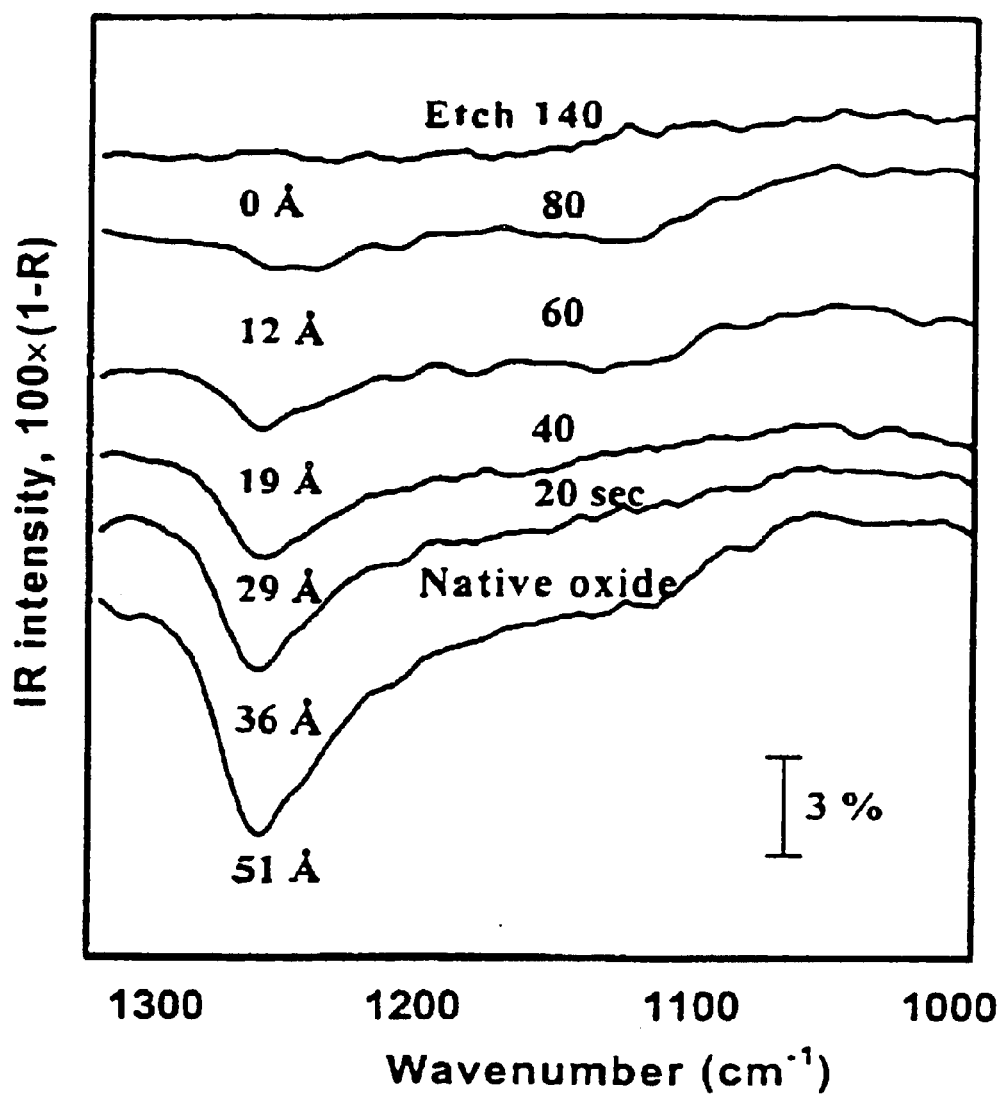
FIG. 4 illustrates MEPR-FTIR spectra of a 50 Å-thick native oxide over a silicon sample during etch back by 1/50 buffered HF ($NH_3F$:HF=10:1).

FIG. 4 shows the MEPR-FTIR spectra of an originally 50-Å thick native oxide; the oxide is etched back in a controlled manner. The LO mode intensity at about 1250 $cm^{-1}$ is probed and studied as a function of the oxide thickness. Other IR features such as the TO mode (at 1050 $cm^{-1}$) and the interstitial oxygen bonding (at 1108 $cm^{-1}$) are removed through the background subtraction outlined above. The longer the etching time, the lower the LO mode intensity, which corresponds to smaller oxide thickness. Also, with decreasing oxide thickness, the LO mode vibrational frequency tends to shift to lower value.

Figure 5:
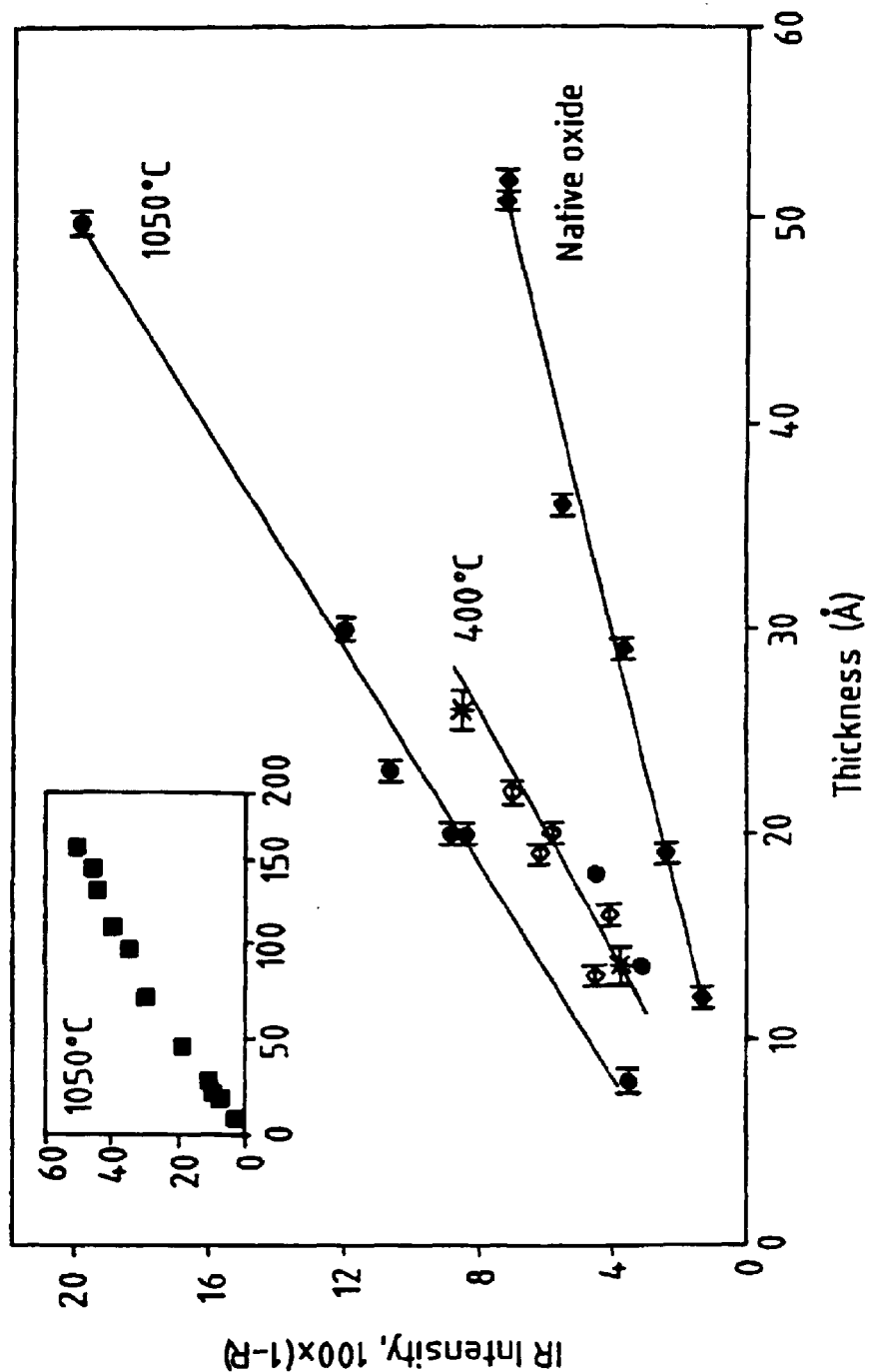
FIG. 5 illustrates data of the LO mode MEPR-FTIR intensity-film thickness relationships for native and thermal oxides formed at 400° C. and 1050° C. in air.

FIG. 5 shows the relationship between the IR intensity and film thickness for oxides formed in different environments. Ellipsometry data is shown for the native oxide (♦), and thermal oxides at 400° C. (◊) and 1050° C. (■). XPS data is shown for the thermal oxide at 400° C. (*). Finally, XTEM data is shown for the thermal oxide at 400° C. (●). Solid lines are regression results with slopes of 0.15 for the native oxide, 0.35 for the thermal oxide formed at 400° C., and 0.39 for the thermal oxide at 1050° C. The inset is for the 1050° C. thermal oxides as thick as 167 Å. The LO mode MEPR intensity is obtained as discussed earlier. It can be seen that for all oxides within the range of 0–50 Å, an almost linear relationship between the IR intensity and oxide thickness is observed. However, over the range of 0 to 167 Å for oxides thermally grown at 1050° C. as shown in the inset graph of FIG. 5, such a relationship starts deviating from being linear. An increase of the oxide formation temperature from room temperature (native oxide) to 400° C. and 1050° C. (thermally grown oxides) results in experimentally determined slopes of the IR intensity-film thickness lines of 0.15, 0.30 and 0.39, respectively. That is, different oxides have different IR intensity-film thickness relationships; in fact, the higher the substrate oxidation temperature, the higher the LO mode intensity-film thickness slope (see FIG. 5).

Figure 6:
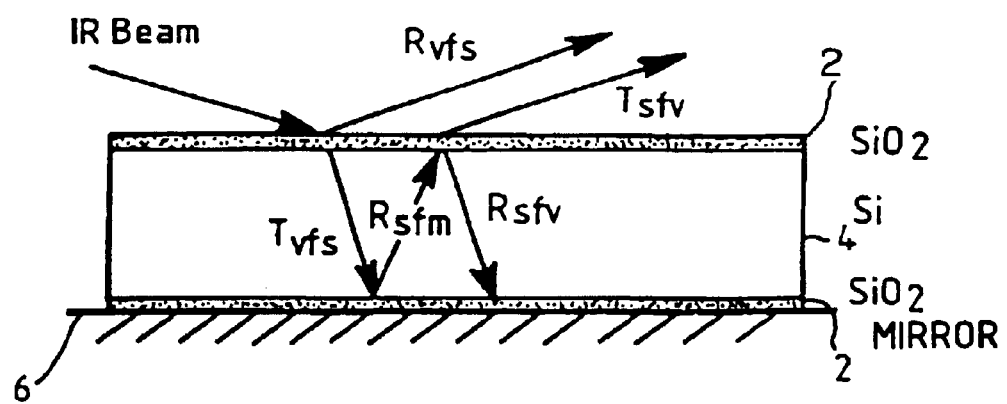
FIG. 6 illustrates schematic optical configuration of MEPR-FTIR for oxide covered silicon wafer samples.

Theoretical calculations on the LO mode MEPR-FTIR intensity-thickness relationship are carried out based on the general Fresnel function. For a P-polarized IR beam, the total reflectance R is the first reflected beam $R_{vfs}$ plus the multiple reflected beams $T_{vfs}R_{sfm}T_{sfv}$, $T_{vfs}R_{sfm}T_{sfv} \cdot (R_{sfv}R_{sfm})$, and so on as illustrated in FIG. 6, where the subscript "vfs" illustrates the sequence of the beam going from vacuum or air, into the film and then to the substrate. Similar sequences are indicated by "sfm" or "sfv", where "m" stands for mirror. The relationships are given as:

$$R = R_{vfs} + \frac{T_{vfs}T_{sfv}R_{sfm}}{1 - R_{sfv}R_{sfm}} \quad (1)$$

where $$R_{vfs} = (1-\alpha)^2 + 2(1-\alpha)(\beta - \alpha \cdot \gamma)\Delta \quad (2)$$

$$\alpha = \frac{2\eta_2}{\eta_0 + \eta_2}$$

$$\beta = \frac{2 \cdot \text{Im}(\varepsilon_1)}{(\eta_0 + \eta_2)}$$

$$\gamma = \frac{\eta_0\eta_2\sin^2\theta_0\text{Im}\left(-\frac{1}{\varepsilon_1}\right) + \text{Im}(\varepsilon_1)}{\eta_0 + \eta_2}$$

$$T_{vfs} = T_0(1 + 2\chi \cdot \Delta) \quad (3)$$

and $$T_0 = \frac{4\eta_0\eta_2}{(\eta_0 + \eta_2)^2}$$

$$\chi = \frac{\left(\eta_0\eta_2\sin^2\theta_0 \cdot \varepsilon_0 \cdot \text{Im}\left(-\frac{1}{\varepsilon_1}\right) + \text{Im}(\varepsilon_1)\right)}{\eta_0 + \eta_2}$$

In the above equations, the following variables denote:
vfs: from vacuum (or air) to film and then to substrate
sfm: from substrate to film and then to mirror sfv: from substrate to film and then to vacuum (or air)

R: reflectance

T: transmittance $\eta_i$: admittance of medium, $\eta_i = N_i/\cos\theta_i$ for P-polarization $N_i$: refractive index of medium i $\theta_i$: angle of incidence or reflection of medium i d: the thickness of the film i=0, 1, 2, for air (or vacuum), thin film, and substrate, respectively $\epsilon_i$: dielectric constant of "i".

Im (I): imaginary part of I $$\Delta = 2\pi d/\lambda$$

$\lambda$: wavelength, and d: the film thickness.

The equations for $R_{sfv}$ and $T_{sfv}$, are the same as those for $R_{vfs}$ and $T_{vfs}$ except that the subscripts "0" and "2" are interchanged. For the reflectance over a mirror surface:

$$R_{sfm} = 1 + \delta \cdot \Delta \quad (4)$$

and $$\delta = 4\sin^2\theta_2 \cdot \eta_2 \cdot \varepsilon_2 \cdot \mathrm{Im}\left(-\frac{1}{\varepsilon_1}\right)$$

In the derivation of equation (1), the silicon wafer is considered to be in a configuration of coherent film/incoherent substrate/coherent film and the bulk silicon substrate is assumed to absorb no IR energy at the silicon oxide LO mode frequency around 1258 cm$^{-1}$. Therefore, the attenuation of intensity by the substrate for one path is considered to be 1, and the interference (phase difference) caused by the bulk silicon wafer is omitted. Over a spectral range from UV to visible and near IR, the substrate absorption should be considered, as shown in the recent improvement on the incoherent reflection from the substrate in ellipsometry. In the derivation of the equations (2)–(4), $\Delta^k$ for $k \geq 2$ is negligible, because the film thickness d ($\geq 50$ Å) is typically much less than the wavelength $\lambda$ (7.9 $\mu$m for the LO mode) used in the calculations.

From equation (1), it can be seen that the IR intensity is a function of film thickness, incident angle and dielectric constant at the absorption frequency of interest. The absorption frequency is 1260 cm$^{-1}$ for the thermal oxide and 1249 cm$^{-1}$ for the native oxide, at which the absolute value of the dielectric constant of these oxides is minimized, respectively.

Figure 7:
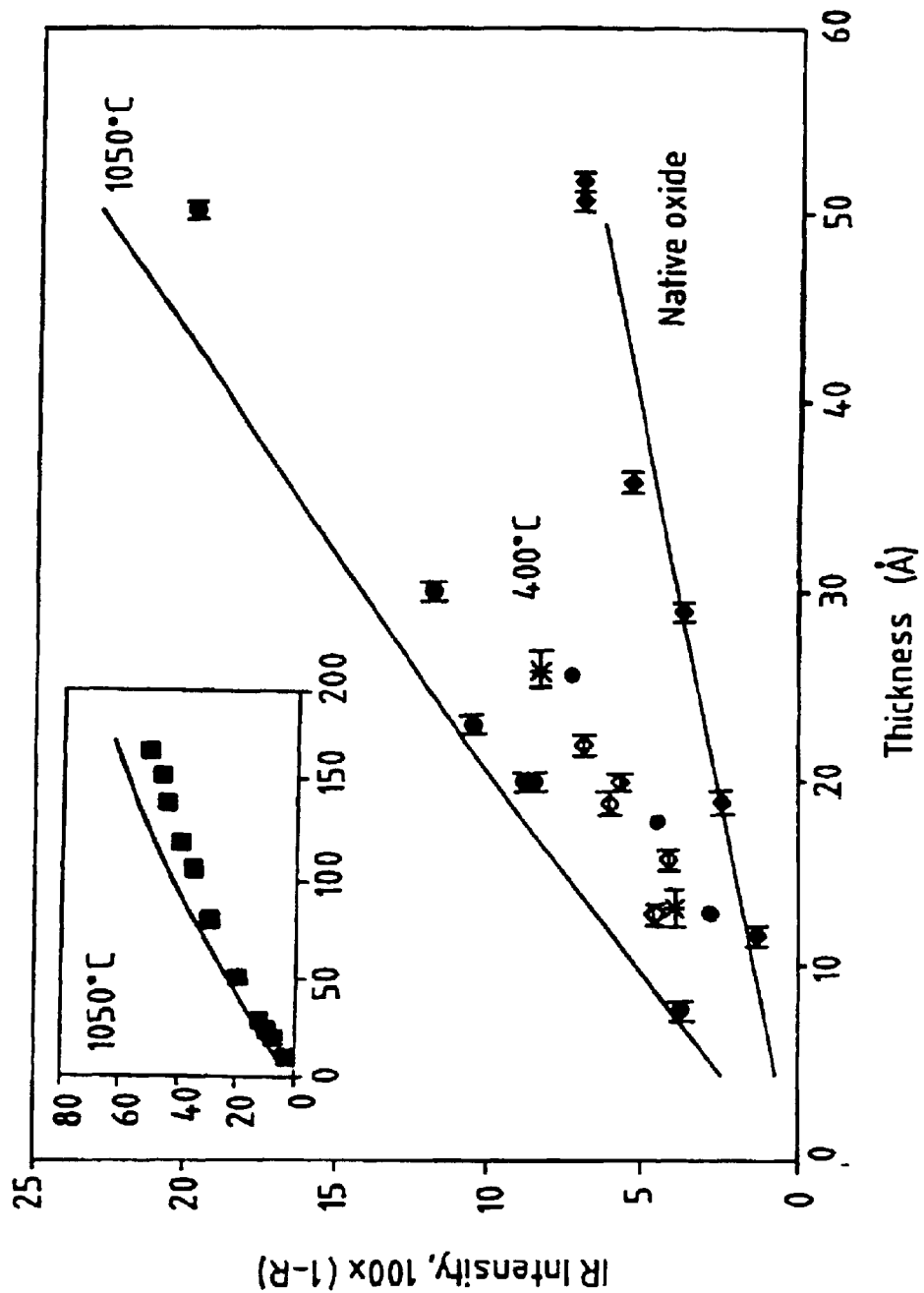
FIG. 7 illustrates experimental data and theoretical calculations (solid lines) for the MEPR-FTIR intensity of the silicon oxide LO mode as a function of film thickness.

FIG. 7 shows experimental data and theoretically predicted results based on Equations (1)–(4) for the MPER-FTIR intensity of silicon oxide LO mode as a function of film thickness. The symbols used are the same as in FIG. 5. It is seen that over the range of 0~50 Å, the theoretically predicted relationships for the thermal oxide grown at 1050° C. and the native oxide are in good agreement with the experimental data. An almost linear relationship is indeed apparent.

For the thicker thermal oxide formed at 1050° C. shown in the inset of FIG. 7, the theoretically calculated relationship between the MEPR intensity and film thickness is found to be non-linear, in agreement with the experimental data. This long-range non-linearity can be further understood through equation (1), which is a polynomial when a Taylor's expansion is applied to the denominator. It is apparent, however, that there is a difference of up to 8% in IR intensity between the theoretically calculated results and the corresponding data for the thicker thermal oxides grown at 1050° C. This difference may be the result of the difference between the real dielectric constant of the oxide formed here (in air at 1050° C. and 167 Å-thick) and the dielectric constant used in the simulation. In this example, the latter is extracted from an oxide thicker than 0.8 $\mu$m, formed in O$_2$ at 1050° C., followed by annealing in N$_2$ for 30 min.

The native and thermal oxides formed at 1050° C. have LO mode IR intensity-film thickness slopes of 0.15 and 0.39, respectively. This shows different properties for such different oxides. There are mainly two parameters affecting the slope: one is the incident angle, and the other is the dielectric constant. Because the incident angle used experimentally and in theoretical calculations (e.g., 80°) is the same, the dielectric constant would have to be different in these two oxides. This is corroborated by studies suggesting that the refractive index of SiO$_2$ changes with film thickness, formation temperature and the stress of the film.

At the absorption frequency of the SiO$_2$ LO mode, it is found that the imaginary part of the dielectric constant, Im ($\epsilon$), changes from 0.6 for a native oxide to 0.3 for a thermal oxide. Similar changes also take place at the energy-loss function, Im ($-1/\epsilon$). These changes are responsible for the different slopes mentioned above. It is conceivable that such a change of the dielectric constant would be continuous, and thus, all oxides formed between room temperature (native oxide) and 1050° C. could have slopes between 0.15 and 0.39. This is based, in part, on the slope of the LO mode intensity-film thickness relationship for the thermal oxide grown at 400° C. that is found to be between those of the native oxides and thermal oxides grown at 1050° C. (see FIG. 5). IR ellipsometry is also effective in determining the dielectric constant over the IR range, as shown in studies of the vibrational properties of hydrogenated amorphous carbon films. Acquisition of the dielectric constant for the oxide formed at 400° C. can then be interpreted in terms of film density using effective medium theories.

An understanding of the IR intensity-thickness relationship is important in applying MEPR-FTIR spectroscopy to the characterization of ultra-thin dielectric films. From the above analyses there is no apparent limitation of the application of MEPR-FTIR to other ultrathin films. There are at least two plausible protocols for the application of such an approach. One is to obtain a data point of the IR intensity and thickness, set up a calibration line, and use that line for other thicknesses. Another protocol could be to form the calibration line theoretically from the corresponding dielectric constant. For the former protocol, the accuracy would depend on two factors: 1) the accuracy of the calibrating data point, and 2) the error resulting from the linear approximation. The maximum uncertainty is, thus, estimated to be about 1±0.2 Å within the range of 0–50 Å. In the latter protocol, the uncertainty would depend on the accuracy of the dielectric constant used.

Similar to single bounce reflectance IR spectroscopy, MEPR-FTIR can also be used for in-situ characterization of other process-property relationships of ultrathin films (<30 Å). In the low temperature oxidation of Si by ozone, for example, MEPR-FTIR spectroscopy can been used in a rapid thermal processing system and several oxide properties have been previously obtained through in-situ analyses of the IR spectral frequencies and intensities.

Previous experimentation has been done by performing IR intensity-film thickness simulation on a SiO$_2$ covered (only on the shining side) one-sided polished wafer (see Fujimura et al., The Physics and Chemistry of SiO$_2$ and the SiO$_2$ Interface 2, Plenum Press, 1993)). Also, Koller et al. (see J. Appl. Phys. 64, 4704 (1988)) reported IR intensity-thickness simulations of PECVD (Plasma Enhanced Chemical Vapor Deposition) SiO$_2$ on Si wafer. Their simulated and experimental results support non-linear relationships for thickness up to 2000 Å. In the latter work, only silicon dioxide on silicon (i.e., without a mirror or polarizer) is simulated.

UV-visible ellipsometry, known for thin film and bulk material characterization, has been used to measure the oxide thickness together with other techniques such as X-ray Photoelectron Spectroscopy (XPS) and cross-sectional transmission election microscopy (XTEM). One advantage of using the proposed MEPR-FTIR method over UV-visible ellipsometry is that the vibrational properties of surfaces and thin films belonging to different species can thus be probed directly with a high sensitivity, while the film thickness is obtained at the same time. Based on the IR spectral intensities, MEPR-FTIR spectroscopy may also have smaller influence from the surface roughness than that affecting the accuracy of UV-visible ellipsometry. Finally, it is pointed out that for an FTIR spectrometer with a sensitivity of 0.01%, MEPR-FTIR spectroscopy could allow submonolayer (down to a small fraction of a monolayer) probing of silicon oxide on Si.

MEPR-FTIR spectroscopy is therefore disclosed for probing film properties of ultrathin gate dielectrics. The mirror-attachment and P-polarization within MEPR-FTIR spectroscopy are shown to increase the intensity of the silicon oxide LO mode by a factor of 20. This enhancement comes from the redirection of the IR beam by the mirror, contributions from both sides of the sample, the P-polarized beam, and the standing electric field caused by the mirror. Such a large enhancement extends in situ-compatible IR reflectance probing to the ultrathin film regime of gate oxides, and it provides information about both film thickness and chemical bonding.

The MEPR-FTIR intensity-thickness relationship is studied both experimentally and theoretically. Over the film thickness range of 0~167 Å, a non-linear relationship is observed, while over the range of 0~50 Å a practically linear relationship is found. The LO mode intensity-film thickness relationships of oxides formed at different temperatures exhibit different slopes, most likely because of the dielectric constant. The agreement between experimental results and theoretical predictions is found to be satisfactory.

An apparatus by which the above-described MEPR-FTIR may be effected will be described in the context of a Rapid Thermal Processing (RTP) system. An important method in probing gas emission is a residual gas analyzer (RGA), which is known for its accuracy in analyzing gas products of chemical reactions. Additionally, a Rapid Thermal Processing (RTP) system equipped with an ellipsometer has previously been reported to be very helpful in investigating CVD (Chemical Vapor Deposition) and silicidation. Therefore, the combination of a RGA with advanced RTP and ozone processing technologies into one system will result in a powerful processing tool for probing most semiconductor thermal processes.

Figure 8:
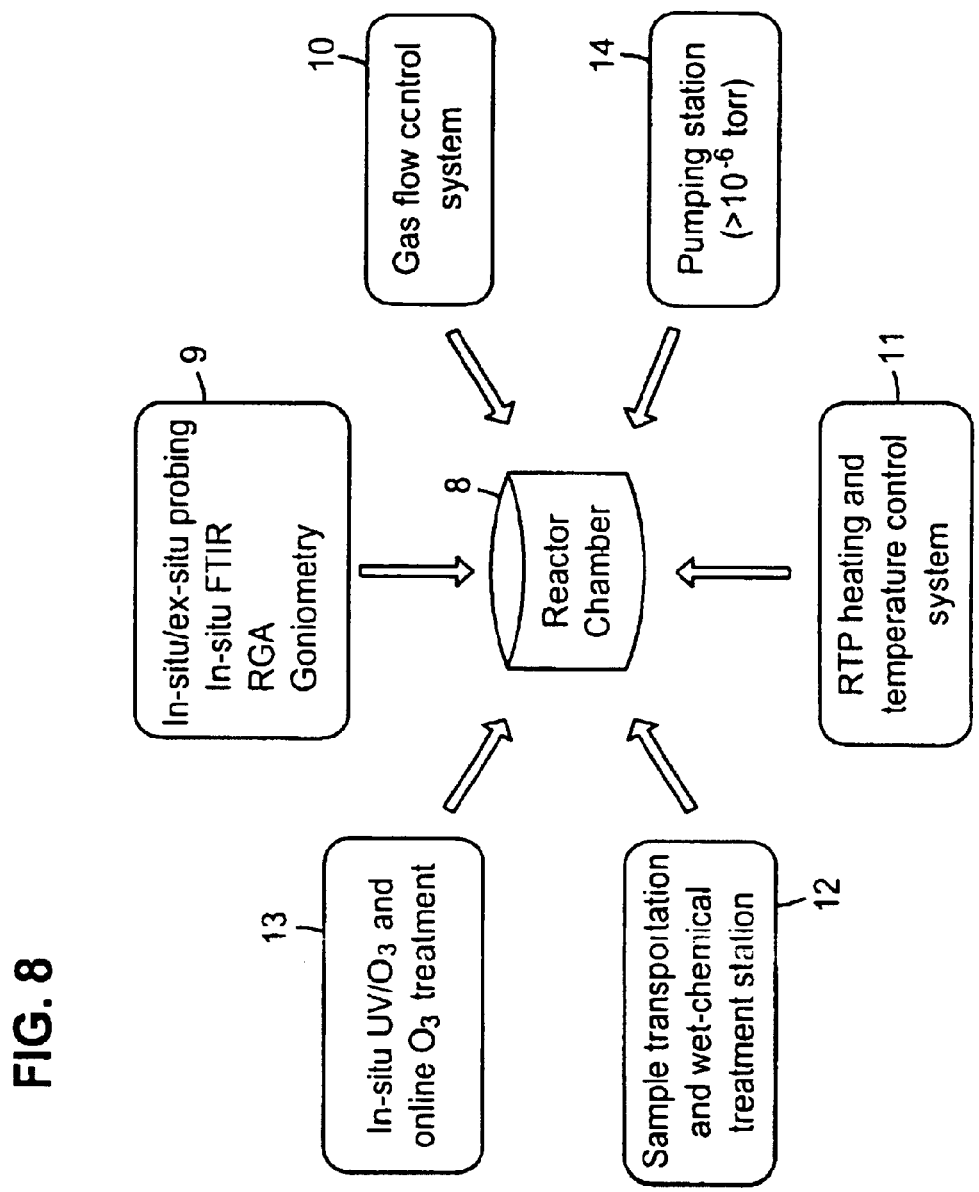
FIG. 8 illustrates a schematic diagram of a rapid thermal processing system according to the teachings of the present disclosure.

An example of a Rapid Thermal RTP system with in-situ FTIR, on-line RGA and in-situ/ex-situ Goniometry and in-situ/online UV-ozone generator is illustrated in FIG. 8 as a schematic block diagram. The system in FIG. 8 consists of seven subsystems: reactor chamber 8, in-situ/ex-situ probing system (FTIR, Goniometry and RGA) 9, gas flow control system 10, RTP heating and temperature control system 11, sample transportation and wet chemical treatment 12, in-situ UV/O$_3$ online O$_3$ treatment system 13, and vacuum system 14. Each of these subsystems will be described in detail in the following discussion.

Figure 9:
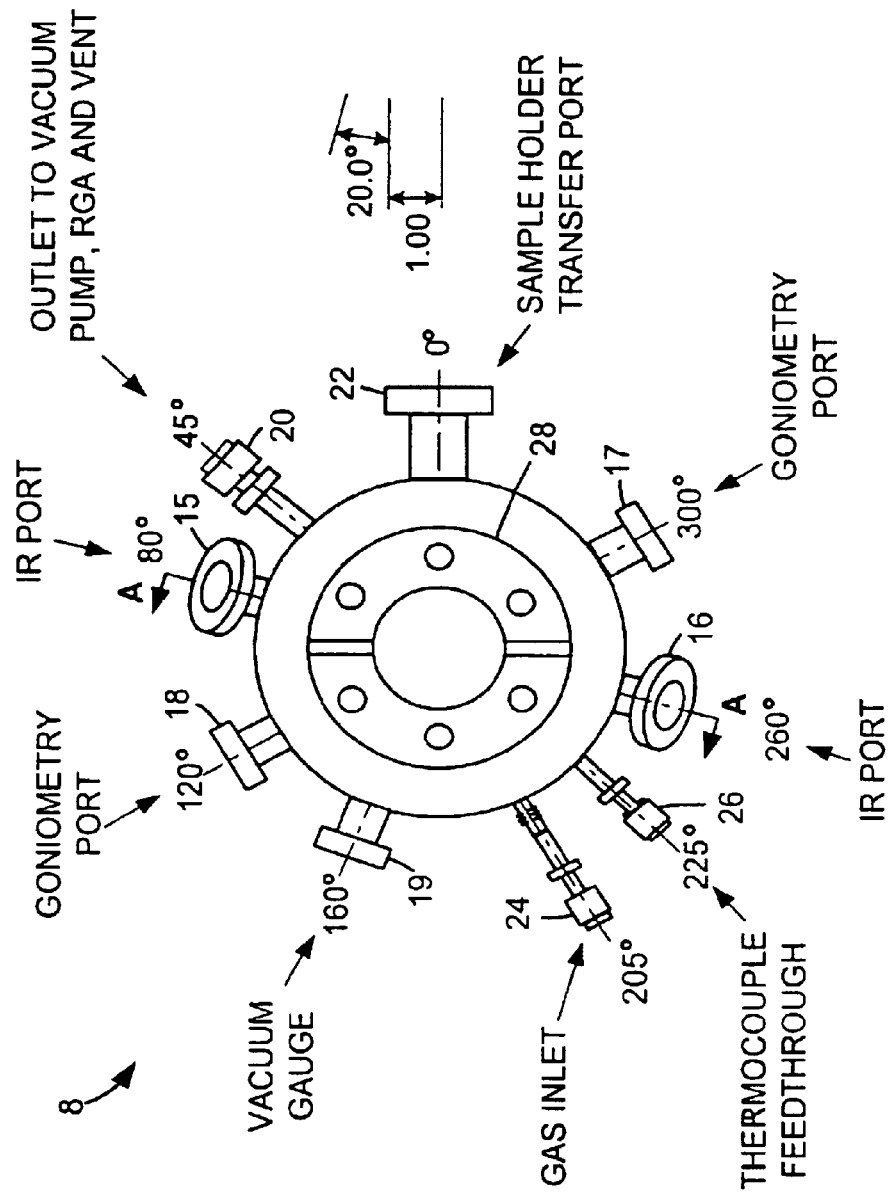
FIG. 9 illustrates a top view of the reactor chamber shown in FIG. 8.

The reactor chamber 8, a top view of which is illustrated in FIG. 9, is specifically made of stainless steel to anticipate for any corrosive chemical environment. In this example, the chamber 8 is cylindrical with a height of approximately 2" and a diameter of approximately 4", but is not limited to only this shape or dimensions. Twelve access openings are distributed on the outer surface of the cylindrical chamber with various operating functions. These openings are shown at various angles relative to zero degrees (shown at the right hand side of the figure indicated in FIG. 9. These angles are by way of example only and the placement of openings is not limited to these specific angles.

Figure 10:
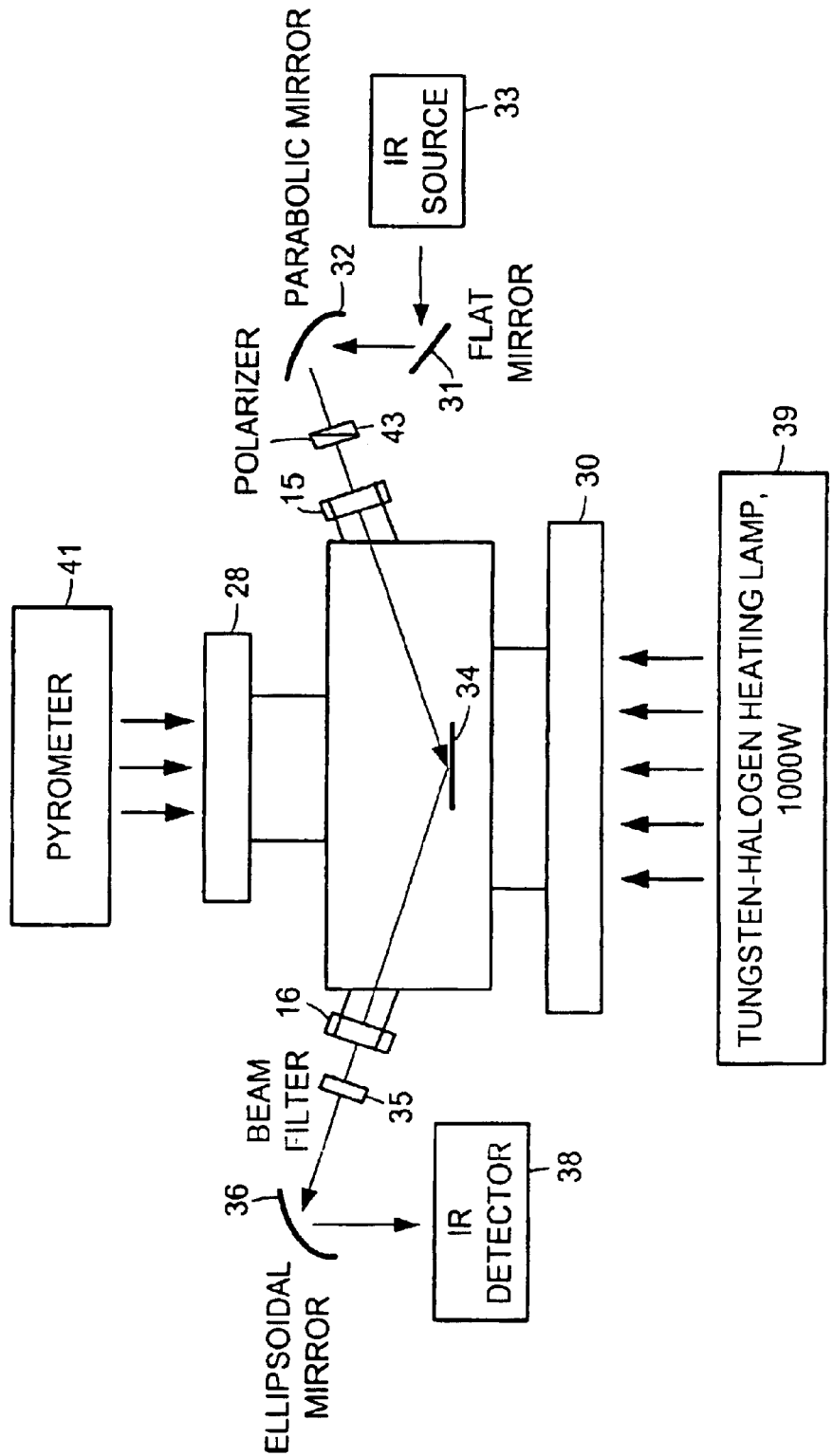
FIG. 10 illustrates a side view of the rapid thermal processing system illustrated in FIG. 8.

Two CF flanges 15 and 16 with an angle of 20° to the horizontal level of the chamber body, for example, are used for in-situ FTIR characterization. They are connected to optical KBr windows (not shown in FIG. 9). These two openings can also be used for in-situ Ellipsometry. Another pair of flanges 17, 18 are used for contact angle measurement and are connected to two conventional optical glass windows. Another flange 19 is connected to a Pirani gauge (vacuum gauge) for vacuum measurement from 760 to 10$^{-2}$ torr, for example. An outlet 20 of the chamber is a swagelok to which a vacuum station, RGA, and exhaust are connected. A larger opening 22 (e.g., a 2¾" flange) on the right hand side of FIG. 9 has two functions. It is used for both sample holding and sample transferring. Three other swageloks 24, 26 (the other is directly under 24 and, thus, cannot be shown in this top view) are used for the thermocouple feedthrough, gas inlet, and contact angle needle transfer (not shown in FIG. 9), respectively. The function of top and bottom flanges 28, 30 (not shown in FIG. 9) is better visualized from the side view of the chamber 1, as shown in FIG. 10.

A top flange opening 28 in FIG. 10 has two functions: one is for the temperature measurement using optical pyrometer, and the other is for the UV assisted radiation treatment by connecting it to the ozone generator 13 (to be discussed later). A bottom flange 30 is connected to a quartz window for the rapid thermal processing by a heating source 39, such as a 1000 W tungsten halogen heating lamp. The IR detection configuration shown in FIG. 10 will be discussed in the directly following discussion.

In this particular example, IR radiation heating was selected as the mode of rapid thermal heating source, but is not limited to only this mode. The heating source 39 may be a tungsten halogen IR lamp parabolic strip heater (e.g., a model 5305-2 parabolic strip heater by Research Inc.). The heating lamp 39 concentrates high radiant flux energy on an approximately 1½" target strip. A parabolic shaped specular aluminum reflector 32 produces a narrow, highly directional heating pattern and directed radiant energy from a high temperature (2200° C.–2900° C.) tungsten filament tubular quartz lamp onto the target strip width. Cooling water may be routed through the reflector body of the lamp holder so that the reflector can be used for a long time. The tungsten halogen lamp 39 is placed into the above heater holder with a true exposed heating length of 2.5". As used in this example, the total exposed heating area of the particular lamp is 3.75 in$^2$. The rated power is, for example, 1000 W at 8.34 A and 120 V. The heat flux output is 255 W per linear inch. Rapid heating of the Si sample is achieved at full power of the lamp, and results in heating rates of over 20° C. per second by the IR lamp. The IR lamp may be controlled by a Model 609 SCR Power Controller made by Research Inc., for example. The maximum current is 20

Amps and can reach full power in 1–2 seconds. In accordance with this design, two feedback controls with thermocouple and pyrometer, and one manual control are installed.

A pyrometer 41 (OS1831-31-C infrared temperature transmitter from OMEGA) may be used for temperature measurement and connected to top flange 28. It has an additional convenience of a built-in digital display for local on-site readings. The temperature range is 300–975° C. The spectral response is specifically chosen to be 3.76–3.88 $\mu$m so that the interference from the IR lamp (~0.5 $\mu$m in wavelength) can be avoided. At this spectral range, a sapphire flange window with emission compensation factor 0.88 is preferred. The distance between the pyrometer and the measured sample is arranged to be 7", where a minimum spot size of 0.5" was obtained.

The detecting limit for the pyrometer is down to 300° C. Hence, for a temperature near that limit, a K-type thermocouple was used. The thermocouple is grounded and shielded with stainless steel. A thin and long thermocouple (at a length of 18" and diameter of 0.010") is preferred for its better contact with wafer samples.

During operation of the illustrated RTP system, the thermocouple feedthrough and KBr optical windows are vulnerable to damage. These two components may be made by gluing a thermocouple to a swagelok for the thermocouple feedthrough and a KBr glass to a flange for the optical window. An epoxi-patch from Hysol Engineering Adhesives (Dexter Corporation) is preferable as the cement because it can maintain a vacuum higher than $10^{-6}$ torr.

When a full power is supplied to the IR heating lamp 39, a temperature as high as 600° C. can be maintained on a silicon wafer at an atmosphere of Argon (Ar) gas. A higher temperature may be achieved under vacuum. Temperatures as high as 700° C. in an Ar gas environment are obtained when another IR lamp is attached to the top window of the chamber via top flange 28 at the sacrifice of using a pyrometer.

Three detecting techniques, FTIR spectroscopy, Goniometry and mass spectrometry from residual gas analyzer (RGA), are equipped in the RTP system and are discussed in the immediately following discussion below.

There are four commonly used FTIR modes: transmission, single beam reflectance, diffusion reflectance and ATR (attenuated total reflectance). Single beam reflectance mode is preferred in the present RTP system because of its in-situ compatibility. As discussed previously, the FTIR spectrometer utilized may be a Nicolet Magna-IR 560, with an internal standard DTGS detector and an external MCT-A detector. The in-situ IR detecting system, shown schematically in FIG. 10, is composed of three mirrors (one flat, another parabolic and the third ellipsoidal), two KBr windows, and an external MCT-A detector (IR spectrum range 650–4000 $cm^{-1}$). The acquisition of in-situ FTIR spectroscopy is comprised of the switching of the FTIR bench and the adjustment of those mirrors and the sample holder as will be discussed later.

The MCT-A liquid nitrogen-cooled detector is attached to the FTIR spectrometer and fully integrated with it through a Nicolet "passport optical system," A mirror or optical direction system inside the FTIR bench, is used to switch the IR beam outside the bench so that external IR detection can be realized. The beam coming out of the IR bench travels to the external IR detector 38 according to the following general sequence: the beam issues from an IR source 33 to a flat mirror 31, to a parabolic mirror 32, through a beam polarizer 43 to a sample 34 (e.g., a 12 inch wafer polished on both sides), reflected off the sample 34 through a KBr window filter 35, to the surface of a sample ellipsoidal mirror 36, and to external MCT-A IR detector 38. The IR signal comes from both the wafer sample 34 and the gas environment en route. It is noted that the shown location of beam polarizer 43 is merely exemplary and may be located in the beam path at any place prior to the sample 34, including within the IR source 33. In setting the mirror system, the IR beam is focused onto the center of the detector's 38 aperture, which can be realized by adjusting the ellipsoidal 36 or parabolic 32 mirror position. This center yields the most intense signal. An IR card, which fluoresces when in contact with IR beam, is also extremely helpful in adjusting the position of mirrors and IR detector. The incident angle of the IR beam to the normal of the sample 34 is set to the Brewster angle of the Si wafer (approximately 73° in this case), at which a high reflection IR intensity may be obtained. After the mirror system is adjusted, the reflection IR signal can be collected.

The procedure for the IR signal collection is as follows. First, the detector 38 is cooled with liquid nitrogen (which is filled into the detector 38 from an opening on top). Then the IR bench is switched from the main bench to the external bench using the FTIR control software such as OMNIC E.S.P. 5.1. After the external IR system is carefully aligned by adjusting mirrors and detector's position, an IR intensity over 10 (expressed as maximum interferogram amplitude) may be obtained. However, such a high IR intensity is more than adequate. Thus, in order to avoid any damage to the detector 38, the beam filter 35 may be selected and put in front of the detector until an IR intensity of about 8 is obtained.

As mentioned previously, the KBr crystal 35, transparent to the infrared radiation, is preferably selected as the window material. It allows 90% of the infrared radiation to be transmitted in a wide frequency range between 4000 and 400 $cm^{-1}$. The KBr crystal can also withstand high temperatures (300° C.) and mechanical shock. This is extremely important in a rapid heating system where sudden changes in temperature occur. However, KBr windows have the disadvantages of being brittle and hygroscopic. For this reason, a standard Conflat flange KBr window, for example, is not commercially available and a specific constructed KBr window is preferable. This optical window may be made as follows. First, a 21 mm diameter bore was drilled in a stainless steel 1⅓" Conflat flange. Then, a KBr crystal (from Spectra-Tech), 20 mm in diameter and 2 mm in thickness, is glued to the flange bore using the epoxy mentioned above. After curing overnight at room temperature, the optical window may be used.

In the particular disclosed example, a Model 102-00 bench telegoniometer with a video camera attachment is used for the in-situ contact angle measurement. An optional auxiliary lens of 165–200 mm is preferable to get a clear view of contact angles for this system. The objective lens is placed close to one of flange openings 17 or 18. Then, a droplet at the size of 6 $\mu$l from liquid, such as water, is formed on the wafer substrate using a micro-syringe that penetrates into the chamber through the swagelok (which was not shown) in the chamber and the image of the droplet is focused by adjusting the image focus dial. An illuminator is then attached to the opposite one of the flange openings 17 or 18 so that the image can be illuminated. The in-situ telegoniometry can give the contact angle value of the sample just after the processing, without moving the sample out of the chamber. As an alternative, a Model 100-00 contact angle goniometer, secluded in an Ar purged plastic bag, may also be used for the contact angle measurement in an ex-situ configuration. The error of contact angles measured from both goniometers is less than 1 degree. The gas phase of a reaction may be sampled by a Stanford Research Systems Residual Gas Analyzer (RGA 200) or an equivalent.

Figure 11:
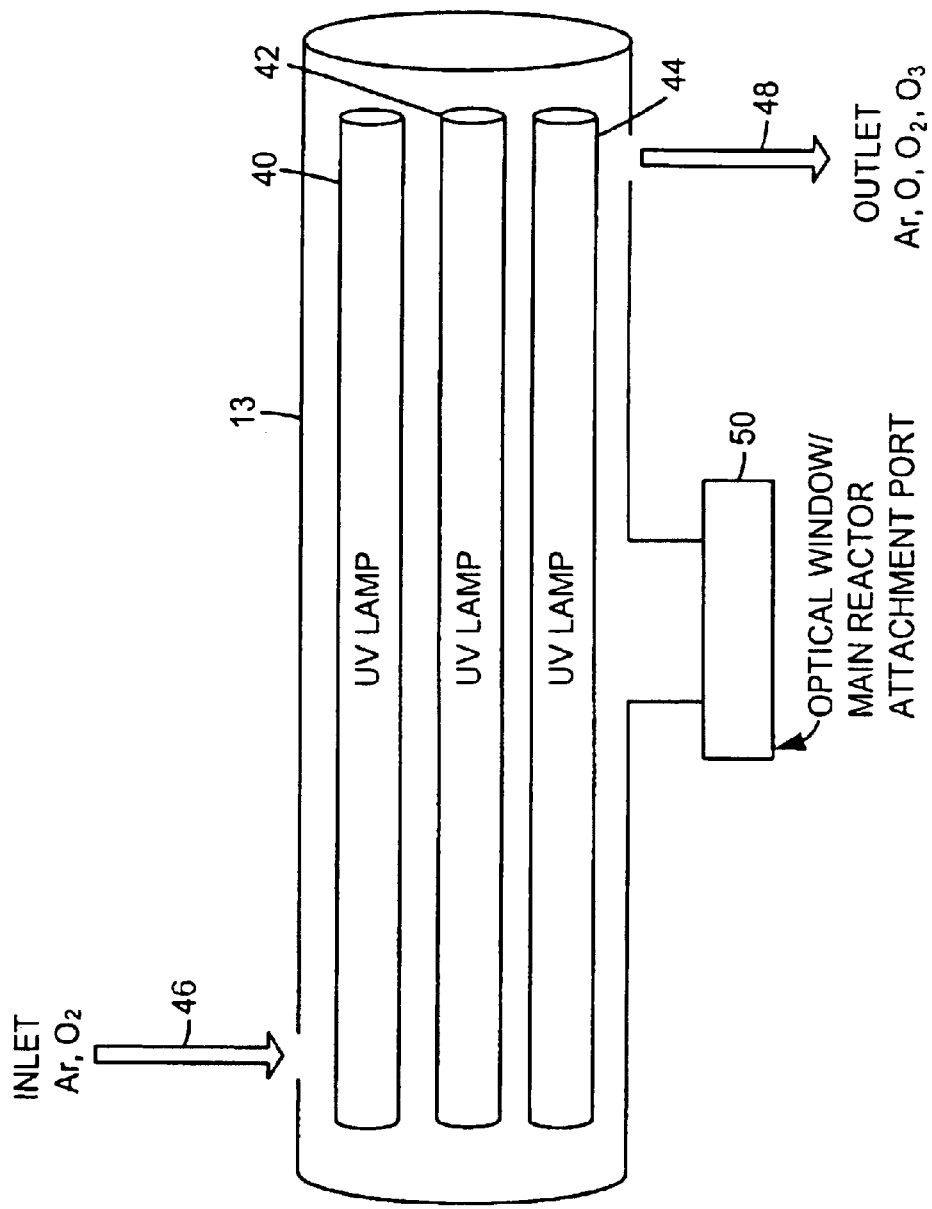
FIG. 11 illustrates a schematic diagram of the ozone generator shown in FIG. 8.

In the RTP System of FIG. 8, ozone is generated by exposing molecular oxygen to UV radiation. FIG. 11 shows a schematic diagram of an example ozone generator 13 that may be used. The generator 13 is a tubular stainless steel reactor that houses three low pressure Hg Ultraviolet lamps 40, 42, 44 (e.g., Bulbtonics PN VOG10T5VH/S400), with four main ports for gas inlet 46, gas outlet 48, an optical window/main reactor attachment port 50, and a feed-through for power supply to the lamps (not shown). The low pressure Hg lamps 40, 42, 44 emit two main frequencies, 185 nm and 254 nm, at a relative intensity ratio of approximately 1:10. The 185 nm UV light is responsible for the generation of ozone gas from $O_2$, while the 254 nm light dissociates ozone gas into $O_2$. More ozone can be generated if the amount of 185 nm radiation line (i.e., ozone generating line) is increased while minimizing the amount of 254 nm light that breaks down ozone. The amount of ozone generated is controlled by regulating the $O_2$ feed and the amount of UV radiation at 185 nm. Normally, a low flow rate of $O_2$ will have a high concentration of $O_3$ at a constant lamp power. When all the three lamps 40, 42, 44 are turned on, an ozone concentration as high as 1500 ppm can be obtained at the pure $O_2$ flowrate of 1 slm. The ozone generator 13 can be operated as an independent unit (referred to as online ozone processing, shown later in the gas flowing system) or it can be attached to the top flange 28 of the reactor chamber 8 for in-situ UV assisted $O_3$ applications. Particularly, in the cases of Si and SiGe oxidation, the online ozone processing is utilized.

The concentration of ozone may be monitored using both a multi-channel Model 450 Ozone Monitor (Advanced Pollution Instruments Inc.) and the in-situ reflectance FTIR mode. The Ozone Monitor detects ozone molecules based on the adsorption of 254 nm UV light that corresponds to an internal electronic resonance of the $O_3$ molecule. Based on external calibration data provided by the manufacturer, the accuracy of the ozone analyzer is less than 1% of the measured value.

Figure 12:
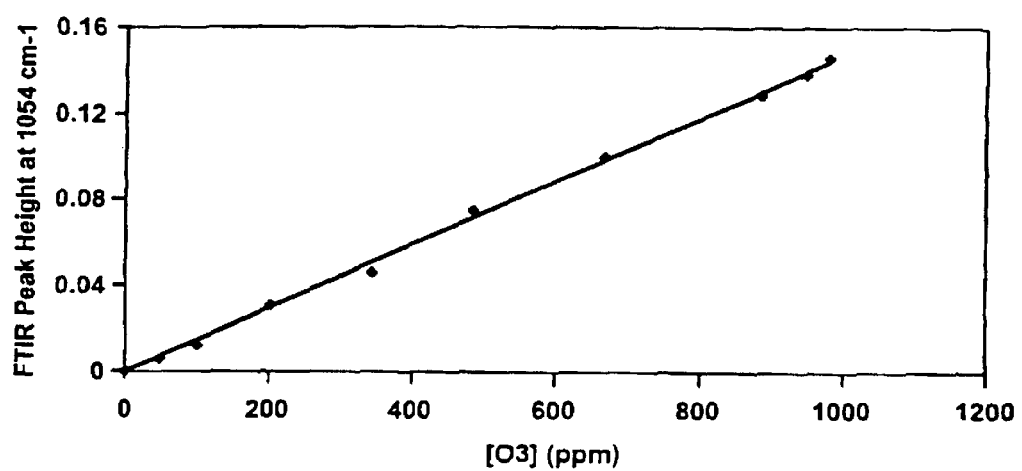
FIG. 12 illustrates an IR response curve for ozone with in-situ reflectance FTIR mode under steady-state ozone conditions.

To directly monitor the ozone concentration inside the main reactor, an in-situ reflectance FTIR mode was employed, as shown in FIG. 10. Preliminary experiments are first performed to calibrate the $O_3$ IR absorption peak at 1058 $cm^{-1}$ to the ozone concentration measured by the external ozone analyzer. The calibration procedure is as follows. First, the external ozone analyzer is connected to the exhaust port of the main reactor. Next, ozone gas from the ozone generator is flown into the reactor and the exhaust concentration is monitored with the external ozone analyzer until a steady state is achieved. At the steady state, a FTIR spectrum is collected to obtain the peak height of the $O_3$ absorption at 1058 $cm^{-1}$. The procedure is repeated for $O_3$ concentration from 1 to 1000 ppm to generate a calibration curve such as that shown in FIG. 12. The IR response is linear over the range of interest (e.g., 1–1000 ppm). During normal sample processing, the in-situ IR signal is used as a direct monitor of the ozone concentration inside the reactor 8 with supporting data obtained from the external ozone monitor.

A sample holder is also provided to hold the wafer sample inside the chamber when the wafer sample is processed. The holder is designed to meet the following criteria:

1. Easy to load and unload the sample;
2. Able to be manipulated easily from outside the chamber so that the sample position can be adjusted and the IR beam reflected from the sample can be exactly focused onto the IR external detector;
3. Reliable physical connection of a thermocouple to the sample surface for the temperature measurement during the processing; and
4. Cost effective.

Figure 13:
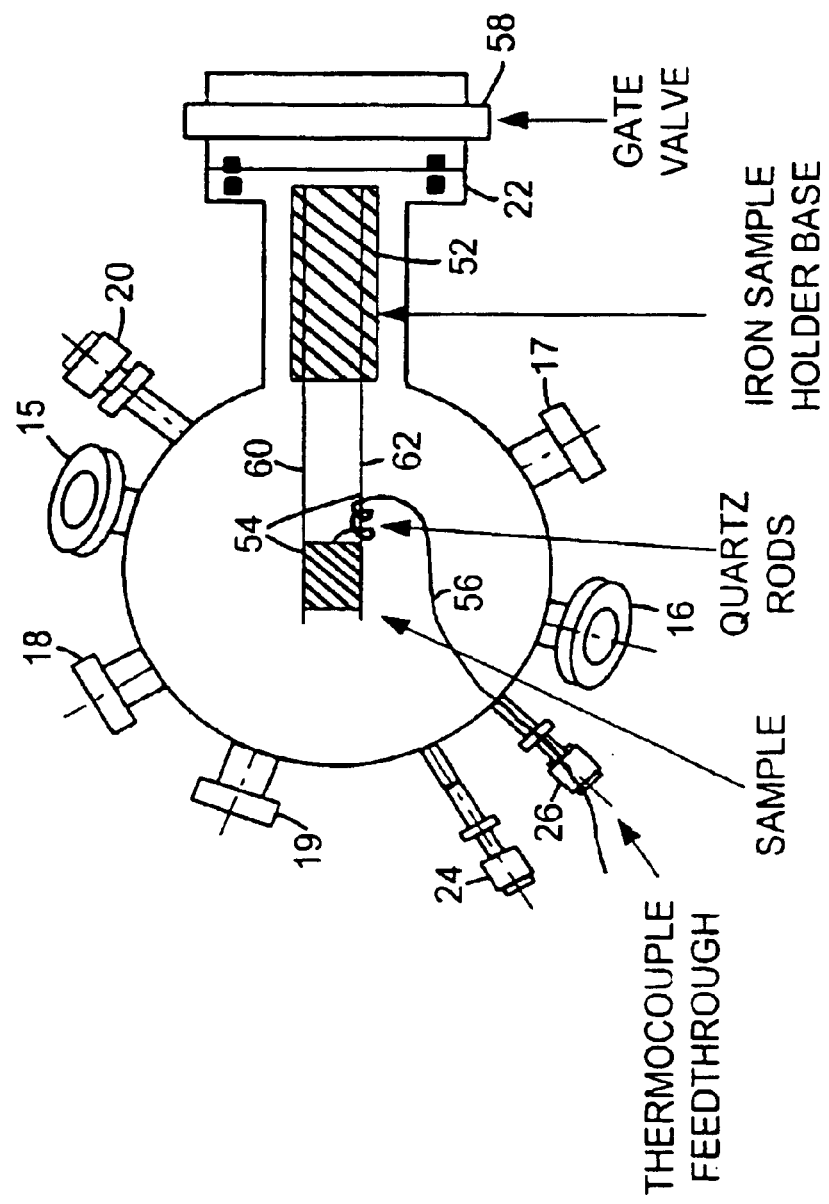
FIG. 13 illustrates a sample holder within the reactor chamber for in-situ reflectance IR spectroscopy.

According to these criteria, a sample holder is constructed, as shown in FIG. 13 from a top-view perspective. The holder is comprised of an iron base 52, a sample susceptor 54, and a thermocouple 56. A wafer sample is physically inserted into the sample susceptor firmly so that a slight movement of the sample holder during the alignment of IR beam will not drop the sample. The sample holder loaded with the wafer sample is moved into and out of the chamber through a high vacuum gate valve 58. The sample susceptor 54 is comprised of two quartz rods 60, 62 and is fixed to the base 52, which is made from iron. Iron provides an opportunity to adjust the sample holder position from the outside of the chamber using a high power magnet. In this way, the reflected IR beam can be aligned. The thermocouple from the 18" long thermocouple feedthrough 26 is swirled or otherwise attached to a quartz rod 60 or 62 and bent over to the wafer surface so that an intense physical contact between the thermocouple end point and the sample surface may be maintained during loading, as well as processing. To minimize any contamination through the gate valve during the loading and unloading, an inner gas protected loading station, made out of a plastic airbag and purged with Ar gas, may be fixed to the gate valve 58. This airbag loading station is a simple load lock, used for both protecting the chamber system during the sample loading and unloading and housing a goniometer for the ex-situ contact angle measurement under a clean and stable inner gas environment.

The above sample holder is used for the normal single beam reflectance mode. As discussed previously, the IR intensity may be enhanced by 20 times using the disclosed mirror enhanced polarized reflectance Fourier transform infrared spectroscopy (MEPR-FTIR). The MEPR-FTIR optimally utilizes an attachment of a mirror to the wafer sample to enhance detection. However, during the thermal processing of the wafer sample it is preferable to have the sample separated from the mirror. This will avoid any suspicious metal contamination from the mirror to the sample. Therefore, another sample holder is provided as shown in FIGS. 14A and 14B.

Figure 14A:
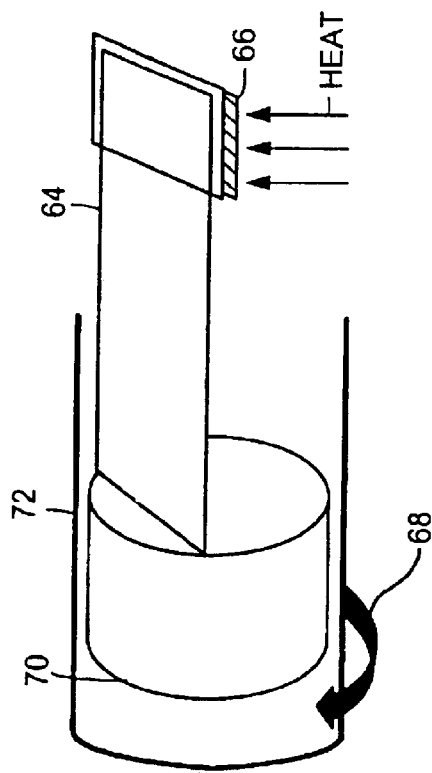
FIG. 14 illustrates a three dimensional view of a sample holder for the MEPR-FTIR mode according to the present teachings.
Figure 14B:
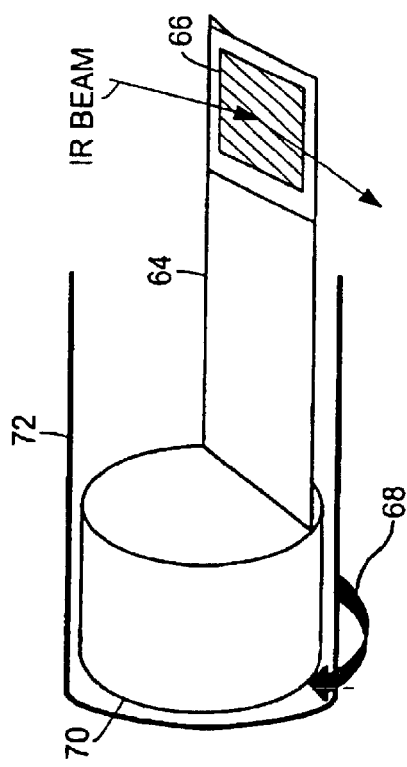

During the detection mode as shown in FIG. 14A, a Si sample 66 rests on top of a platinum (Pt) mirror 64. During the heating mode as shown, however, the sample is suspended away from the Pt mirror at a certain distance because of gravity and is heated by the IR beam that is directed from the bottom of the chamber. A magnetic field source (not shown) effecting magnetic field 68 is used to transfer the sample holder between heating mode and detecting mode by rotating iron base 70 within a guide or housing 72.

In practice, both the disclosed sample holders of FIGS. 13 and 14A and B meet the above design criteria, especially in the aspects that they are easy to operate and extremely cost effective.

As mentioned above, optimization of MEPR-FTIR Spectroscopy utilizes an attachment of a mirror to the wafer sample to enhance detection. Alternatively, however, the wafer sample may be located approximately within a few millimeters (e.g., 3 mm or less) of the mirror and still achieve a beneficial increase in the IR intensity detected. By not attaching the mirror during in-situ processing, for example, the sample will not risk suspicious metal contamination, in-situ processing speeds can be maintained at a higher level and costs minimized, accordingly. In this case, the susceptors shown in FIGS. 13 and 14 may be configured to hold the wafer sample at a fixed distance from the mirror. Additionally, the sample susceptor may be alternatively configured to vary the proximity of the semiconductor wafer to the mirror, affording variable selection of the desired level of IR enhancement.

Although most of thermal processes are carried out at atmospheric pressure or under rough vacuum (~1 torr), the possibility of operating the chamber shown in FIG. 9 under medium or high vacuum for the purpose of cleaning or special treatment is also contemplated. For this reason, the chamber 8 is designed for a vacuum of over $10^{-6}$ torr.

Figure 15:
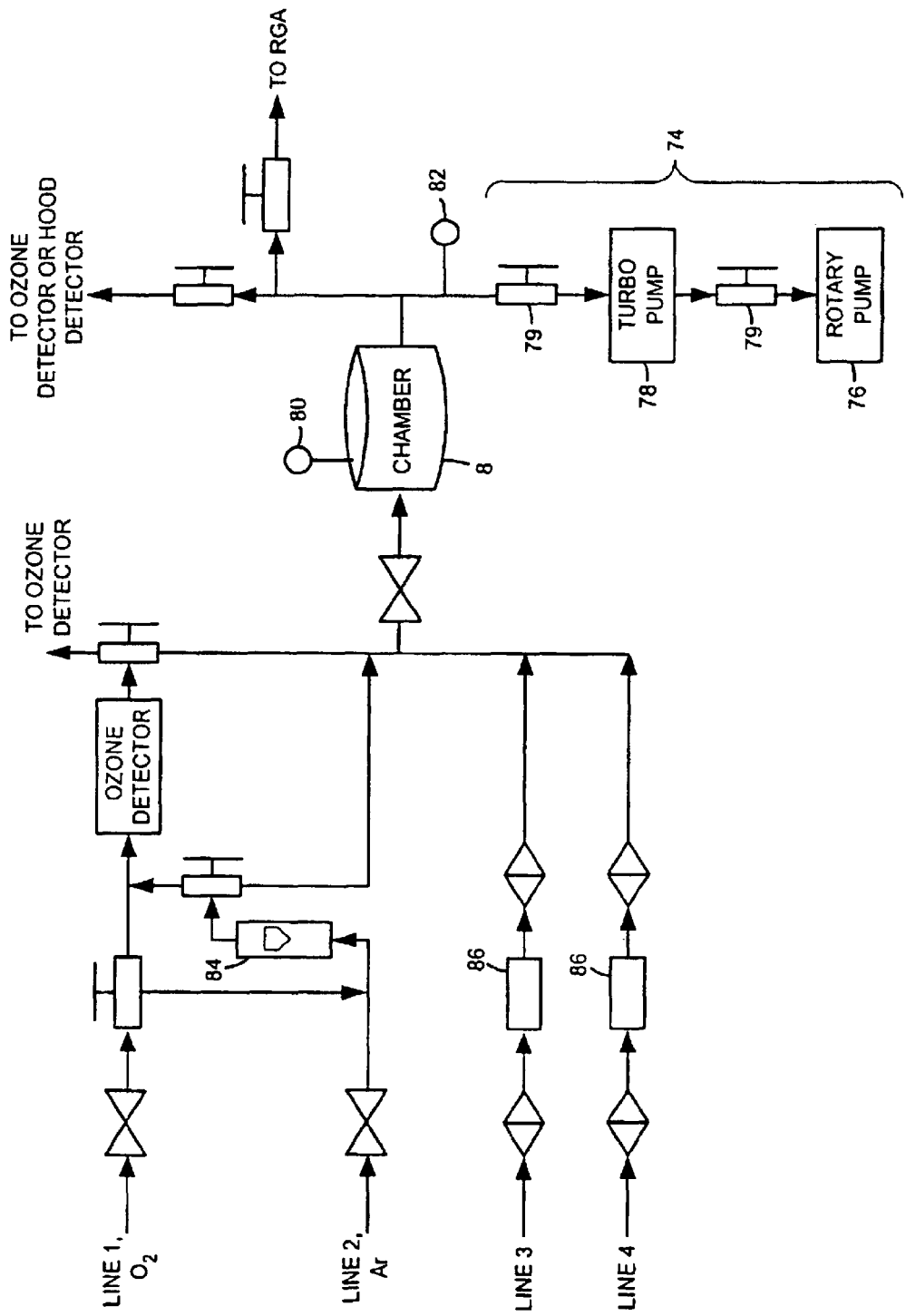
FIG. 15 illustrates a configuration of the gas flowing and pumping system illustrated in FIG. 8.

An example schematic diagram of the pumping station and the gas flowing system is illustrated in FIG. 15. A pumping station 74 comprised of a rotary pump 76 (for vacuum of ~$10^{-3}$ torr) and a turbomolecular pump 78 (for vacuum of ~$10^{-6}$ torr) is used to evacuate the chamber via outlet 20. The rotary pump 76 may be, for example, from Rotary Vacuum Pumps, Inc., with a power of ¼ h.p. The turbomolecular pump 78, may be from Leybold Vacuum Products Inc. (e.g., Turbovac NT 50). A vacuum as high as $2 \times 10^{-6}$ torr is easily achieved after the chamber is baked, evidencing that the system is leakproof. Each of the pumps 76, 78 has an associated vacuum valve 79. Before running any test, the whole system is evacuated to at least $2 \times 10^{-6}$ torr to remove any potential contamination from the background. A Pirani gauge 80 and a Cold Cathode gauge 82 (e.g., a SensaVac Series 953) may be used for monitoring the chamber vacuum via inlet 18.

Gases can be sent into the chamber system through four different lines. Equipped with a ball flowmeter 84, lines 1 and 2 are for gases such as $O_2$ and Ar at high flow rates (0.1–1 slm). Lines 3 and 4 have online mass flow controllers (MFC) 86 from Unit Instruments, Inc. and are optimal for lower gas flow rates (<0.1 slm), especially during chemical vapor deposition. In the Si and SiGe oxidation in $O_3$, line 1 is fed with $O_2$ and ozone gas generated from the online ozone generator 13 and sent to the chamber 8. Line 2, fed with Ar, is used as a purging gas or dilute gas. The configuration of FIG. 15 has proven to be convenient and effective for stabilizing the ozone generator 13 and obtaining a feed with a stable ratio of ozone to molecular oxygen. For the in-situ UV assisted $O_3$ application, the main flowchart is the same except that the ozone generator 13 is attached onto the top of the chamber 8. A fused silica window (not shown) is mounted between the openings at the bottom of the ozone generator 13 and on top of the main reactor. The fused silica window is employed to allow the UV radiation (generated by the lower pressure Hg lamps) to shine onto the sample surface.

An advantageous RTP system has been disclosed in the foregoing discussion. This RTP may be utilized to exploit a variety of semiconductor thermal processes such as thin film oxidation, nitridation, CVD and surface cleaning.

Although certain methods and apparatus may be constructed in accordance with the teachings of the present disclosure, the scope of the coverage of this patent application is not limited thereto. On the contrary, this patent covers all embodiments of the teachings of the invention falling within the scope of the appended claims either literally or under the doctrine of equivalents.

What is claimed is:

1. An apparatus for characterization of a film on a substantially flat semiconductor wafer comprising:

a reactor chamber having a plurality of access openings;

a wafer holder configured to hold the semiconductor wafer, the holder being disposed within the reactor chamber;

a mirror attached to a first surface of the semiconductor wafer;

an infrared light source emitting an infrared light beam;

a beam polarizer disposed in a path of the infrared light beam to polarize the beam;

an optical direction system configured to direct the infrared light beam from the infrared light source through the beam polarizer and a first opening of the plurality of access openings into the reactor chamber toward a second surface of the semiconductor wafer and direct at least a portion of the infrared light that is reflected from the second surface of the film passing through a second opening of the plurality of access openings to outside of the reactor chamber; and an optical detector receiving that at least a portion of the infrared light beam directed by the optical direction system to the optical detector; the optical detector being configured to perform Fourier Transform Infrared Spectroscopy on the received portion of the infrared light beam in order to determine characteristics of the film.

2. A semiconductor processing system for processing the semiconductor wafers employing the apparatus according to claim 1, wherein the apparatus is utilized to perform in-situ characterization analysis of the semiconductor wafers.

3. The apparatus according to claim 1, wherein the optical direction system is further configured to direct the infrared beam such that the beam impinges on the second surface of the semiconductor wafer at a predetermined angle from the normal of the second surface.

4. The apparatus according to claim 3, wherein the predetermined angle is approximately the Brewster angle.

5. The apparatus according to claim 1, wherein the film comprises a thin oxide film.

6. The apparatus according to claim 5, wherein the thin oxide film comprises one of $SiO_2$, $Si_3N_4$, $SiN_xO_y$ and $Ta_2O_5$.

7. The apparatus according to claim 5, wherein the thin oxide film is approximately 50 Δ or less.

8. The apparatus according to claim 1, wherein the film comprises one or more thin oxide films that are disposed on the first and second sides of the semiconductor wafer.

9. The apparatus according to claim 1, wherein the semiconductor wafer is a substantially flat, double-sided polished wafer.

10. The apparatus according to claim 1 wherein the mirror is comprised of platinum.

11. The apparatus according to claim 1, wherein the characterization includes at least one of film thickness determination, film composition determination, film impurities determination, film uniformity determination, surface roughness, and film quality determination.

12. The apparatus according to claim 1, wherein the semiconductor wafer comprises twelve inch silicon wafer having crystallographic directions of 100.

13. An apparatus for characterization of a film on a substantially flat semiconductor wafer comprising:

a reactor chamber having a plurality of access openings:

a wafer holder configured to hold the semiconductor wafer, the holder being disposed within the reactor chamber;

a mirror attached to a first surface of the semiconductor wafer;

an infrared light source emitting an infrared light beam;

a beam polarizer disposed in a oath of the infrared light beam to polarize the beam;

an optical direction system configured to direct the infrared light beam from the infrared light source through the beam polarizer and a first opening of the plurality of access openings into the reactor chamber toward a second surface of the semiconductor wafer and direct at least a portion of the infrared light that is reflected from the second surface of the film passing through a second opening of the plurality of access openings to outside of the reactor chamber;

an optical detector receiving that at least a portion of the infrared light beam directed by the optical direction system to the optical detector; the optical detector being configured to perform Fourier Transform Infrared Spectroscopy on the received portion of the infrared light beam in order to determine characteristics of the film;

a rotatable base with the mirror attached thereto;

a magnetic field generation device configured to selectively rotate the base between at least two first and second indexed positions; and a holding device disposed on the mirror that is configured to hold the wafer in a first position when the base is in the first indexed position and hold the wafer in a second position when the base in the second indexed position.

14. The apparatus according to claim 13, wherein the second position in which the wafer is held by the holding device comprises a separation between the wafer and the mirror.

15. The apparatus according to claim 14, wherein the separation is effected by gravity where the holding device allows the wafer to fall a predetermined distance when the base is moved to the second indexed position.

16. The apparatus according to claim 13, wherein the based is disposed in the first indexed position during a wafer characterization phase and disposed in the second indexed position during a wafer heating phase of in-situ processing of the semiconductor wafer.

17. An apparatus for characterizing films disposed on double-sided polished semiconductor wafers comprising:

a reactor chamber having a plurality of access openings;

a susceptor configured to hold the semiconductor wafer within the reactor chamber;

a mirror disposed in close proximity to a first surface of the semiconductor wafer;

an infrared light source emitting an infrared light beam;

a beam polarizer disposed in a path of the infrared light beam to polarize the beam;

an optical direction system configured to direct the infrared light beam from the infrared light source through the beam polarizer and a first opening of the plurality of access openings into the reactor chamber toward a second surface of the semiconductor wafer and direct at least a portion of the infrared that is reflected from the second surface of the film passing through a second opening of the plurality of access openings to outside of the reactor chamber; and an optical detector receiving that at least a portion of the infrared light beam directed by the optical direction system to the optical detector; the optical detector being configured to perform Fourier Transform Infrared Spectroscopy on the received portion of the infrared light beam in order to determine characteristics of the film.

18. The apparatus according to claim 17, wherein the semiconductor wafer is disposed at a proximity of approximately 3 millimeters or less from the mirror.

19. The apparatus according to claim 17, wherein the susceptor is configured to vary the proximity of the semiconductor wafer to the mirror.

20. The apparatus according claim 17, wherein the susceptor is configured to hold the semiconductor wafer at a fixed distance from the mirror.

21. A method for determining characteristics of a thin film disposed on semiconductor wafer using spectroscopy comprising:

disposing a flat mirror on a first side of the semiconductor wafer;

directing a polarized infrared light beam from an infrared light source to a second side of the semiconductor wafer which at least has the thin film disposed thereon at a predetermined angle with respect to the normal of the second side;

detecting at least a portion of the infrared light beam that is reflected and emanates from the second side of the semiconductor wafer; and performing Fourier Transform Infrared spectroscopy on the portion of the infrared light beam detected in order to determine characteristics of the thin film disposed on the semiconductor wafer.

22. The method according to claim 21, wherein the semiconductor wafer is a twelve inch wafer.

23. The method according to claim 21, wherein the semiconductor wafer is a double-sided polished wafer that is polished on the first and second sides.

24. The method according to claim 23, wherein the film is disposed on the first and second sides of the wafer.

25. The method according to claim 21, wherein determined characteristics includes at least one of film thickness, film composition, film impurities, film uniformity, surface roughness, and film quality.

26. The method according to claim 21, wherein disposing a mirror to the first side increases an intensity of the reflected infrared beam emanating from the second side of the semiconductor wafer.

27. The method according to claim 21, wherein the method is performed in-situ during processing of the semiconductor wafer in a rapid thermal processing system.

28. The method according to claim 27, further comprising:

selectively separating the mirror from the first side of the semiconductor during a portion of the processing of the semiconductor wafer.

29. A method for determining characteristics of a thin film disposed on semiconductor wafer using spectroscopy comprising:

disposing a flat mirror in close proximity with a first side of the semiconductor wafer;

directing a polarized infrared light beam from an infrared light source to a second side of the semiconductor wafer which at least has the thin film disposed thereon at a predetermined angle with respect to the normal of the second side;

detecting at least a portion of the infrared light beam that is reflected and emanates from the second side of the semiconductor wafer; and performing Fourier Transform Infrared spectroscopy on the portion of the infrared light beam detected in order to determine characteristics of the thin film disposed on the semiconductor wafer.

30. The method according to claim 29, wherein the mirror is selectively placeable at varying distances from the first side of the semiconductor wafer.

31. The method according to claim 29, wherein the mirror is placed at distances approximately three millimeters or less from the first side of the semiconductor wafer.

32. An apparatus for characterization of a film on a substantially flat semiconductor wafer comprising:

a reactor chamber having a plurality of access openings;

a wafer holder configured to hold the semiconductor wafer, the holder being disposed within the reactor chamber;

a mirror maintained adjacent a first surface of the semiconductor wafer;

an infrared light source arranged to emit an infrared light beam;

a beam polarizer disposed in a path of the infrared light beam and arranged to polarize the beam;

an optical direction system configured to direct the infrared light beam from the infrared light source through the beam polarizer and through a first one of the plurality of access openings and into the reactor chamber toward a second surface of the semiconductor wafer, the optical direction system further configured to direct at least a portion of the infrared light reflected from the second surface of the film passing through a second opening of the plurality of access openings to outside of the reactor chamber; and an optical detector receiving at least a portion of the infrared light beam directed by the optical direction system to the optical detector; the optical detector being configured to perform Fourier Transform Infrared Spectroscopy on the received portion of the infrared light beam in order to determine the characterization of the film, the characterization of the film including at least one of film thickness, film composition, film impurities, film uniformity, surface roughness, and film quality.

* * * * *

UNITED STATES PATENT AND TRADEMARK OFFICE
CERTIFICATE OF CORRECTION

PATENT NO.    : 6,818,894 B2
DATED         : November 16, 2004
INVENTOR(S)   : Christos G. Takoudis et al.

It is certified that error appears in the above-identified patent and that said Letters Patent is hereby corrected as shown below:

Column 18,
Line 10, delete "according claim 17" and insert instead -- according to claim 17 --.

Signed and Sealed this

Seventeenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,818,894 B2
DATED : November 16, 2004
INVENTOR(S) : Christos G. Takoudis et al.

It is certified that error appears in the above-identified patent and that said Letters Patent is hereby corrected as shown below:

Column 1,
Line 14, insert heading -- GOVERNMENT INTEREST --.
Line 15, insert the following statement -- This invention was made with government support under NSF Grant 9813984 awarded by the National Science Foundation. The government has certain rights in the invention. --.

Column 16,
Line 3, delete "openings:" and insert instead -- openings; --.

Column 17,
Line 10, delete "oath" and insert instead -- path --.

Signed and Sealed this

Sixth Day of September, 2005

JON W. DUDAS
*Director of the United States Patent and Trademark Office*